United States Patent
Woodburn

(10) Patent No.: US 12,233,279 B2
(45) Date of Patent: Feb. 25, 2025

(54) DEVICE FOR PHOTO-THERAPY AND USE THEREOF

(71) Applicant: Tcellerate LLC, Stamford, CT (US)

(72) Inventor: William Woodburn, Greenwich, CT (US)

(73) Assignee: Icahn School of Medicine at Mount Sinai, Greenwich, CT (US)

( * ) Notice: Subject to any disclaimer, the term of this patent is extended or adjusted under 35 U.S.C. 154(b) by 294 days.

(21) Appl. No.: 17/646,613

(22) Filed: Dec. 30, 2021

(65) Prior Publication Data

US 2022/0118276 A1 Apr. 21, 2022

Related U.S. Application Data

(63) Continuation-in-part of application No. 16/168,768, filed on Oct. 23, 2018, now Pat. No. 11,273,320, which is a continuation-in-part of application No. 15/608,588, filed on May 30, 2017, now Pat. No. 10,155,122.

(51) Int. Cl.
*A61N 5/06* (2006.01)

(52) U.S. Cl.
CPC .... *A61N 5/0613* (2013.01); *A61N 2005/0651* (2013.01); *A61N 2005/0654* (2013.01); *A61N 2005/0663* (2013.01)

(58) Field of Classification Search
CPC .......... A61N 5/0613; A61N 2005/0651; A61N 2005/0654; A61N 2005/0663
See application file for complete search history.

(56) References Cited

U.S. PATENT DOCUMENTS

| | | | |
|---|---|---|---|
| 3,986,513 | A | 10/1976 | Stuhl |
| 4,309,616 | A | 1/1982 | Wolff |
| 4,444,189 | A | 4/1984 | Seiverd |
| 6,269,818 | B1 | 8/2001 | Lui et al. |

(Continued)

FOREIGN PATENT DOCUMENTS

| | | |
|---|---|---|
| CN | 103961803 A | 8/2014 |
| CN | 107281649 B | 9/2020 |

(Continued)

OTHER PUBLICATIONS

Brueckmann, "Medium-dose ultraviolet A1 photolherapy in transient acanlholylic dermatosis (Grover's disease)," U. Am. Acad. Dermatol., 52(1):169-170 (Jan. 2005).

(Continued)

*Primary Examiner* — Lynsey C Eiseman
*Assistant Examiner* — Skylar Lindsey Christianson
(74) *Attorney, Agent, or Firm* — Fox Rothschild LLP

(57) ABSTRACT

A method for treating a medical condition in a patient in need thereof is provided. The method includes applying light to the patient thereby stimulating the immune system of the patient, wherein the applying includes irradiating substantially the entire body of the patient with high intensity blue light having a wavelength, intensity, and duration configured to provide immune system stimulation sufficient to treat the medical condition, the stimulation including increasing the population of T-cells in the patient's bloodstream to treat the medical condition. Also included is a method for activating T cells in a subject in need thereof.

21 Claims, 13 Drawing Sheets

(56) References Cited

U.S. PATENT DOCUMENTS

| | | |
|---|---|---|
| 6,290,713 B1 | 9/2001 | Russell |
| 6,896,693 B2 | 5/2005 | Sullivan |
| 7,066,941 B2 | 6/2006 | Perricone |
| 9,463,333 B2 | 10/2016 | Wagenaar Cacciola et al. |
| 2002/0029071 A1 | 3/2002 | Whitehurst |
| 2002/0145859 A1 | 10/2002 | Chubb et al. |
| 2002/0198575 A1 | 12/2002 | Sullivan |
| 2004/0093043 A1 | 5/2004 | Edel et al. |
| 2004/0122492 A1 | 6/2004 | Harth |
| 2005/0093485 A1 | 5/2005 | Spivak |
| 2006/0293727 A1 | 12/2006 | Spooner et al. |
| 2007/0208395 A1 | 9/2007 | Leclerc |
| 2007/0208397 A1 | 9/2007 | Gardner |
| 2007/0233209 A1 | 10/2007 | Whitehurst |
| 2008/0065056 A1 | 3/2008 | Powell et al. |
| 2008/0125834 A1 | 5/2008 | Hendrix et al. |
| 2009/0005838 A1 | 1/2009 | Wagenaar-Cacciola et al. |
| 2009/0247932 A1 | 10/2009 | Barolet |
| 2010/0063487 A1 | 3/2010 | Van Straalen |
| 2010/0069898 A1 | 3/2010 | O'Neil et al. |
| 2010/0179622 A1 | 7/2010 | Wagenaar Cacciola et al. |
| 2011/0060266 A1* | 3/2011 | Streeter ............... A61N 5/0613 604/20 |
| 2012/0101557 A1 | 4/2012 | Wagenaar Cacciola et al. |
| 2012/0245658 A1* | 9/2012 | Pan ..................... A61P 25/00 564/8 |
| 2012/0310307 A1 | 12/2012 | Zhou |
| 2015/0112411 A1 | 4/2015 | Beckman et al. |
| 2016/0008623 A1 | 1/2016 | Jones et al. |
| 2016/0027282 A1 | 1/2016 | Lee |
| 2016/0101294 A1 | 4/2016 | Sun et al. |
| 2016/0175608 A1 | 6/2016 | Livingston |
| 2016/0175609 A1 | 6/2016 | Dye et al. |
| 2016/0331993 A1 | 11/2016 | Moyer |
| 2017/0080246 A1 | 3/2017 | Knight |
| 2017/0216616 A1 | 8/2017 | Boyajian et al. |
| 2019/0054310 A1 | 2/2019 | Woodburn |
| 2021/0290970 A1* | 9/2021 | Hunter ................ A61N 1/403 |
| 2022/0118276 A1 | 4/2022 | Woodburn |

FOREIGN PATENT DOCUMENTS

| | | |
|---|---|---|
| EP | 2044973 A1 | 4/2009 |
| EP | 3354316 A1 | 8/2018 |
| WO | 2009125338 A1 | 10/2009 |
| WO | 2017016315 A1 | 2/2017 |
| WO | 2019206848 A1 | 10/2019 |

OTHER PUBLICATIONS

Liebmann el al., "Blue-Light Irradiation Regulates Proliferation and Differentiation in Human Skin Cells," Journal of Invesligalive Dermatology, 130:259-269 (Jan. 2010).

Phan et al., "Intrinsic Photosensitivity Enhances Motility of T Lymphocytes," Scientific Reports, 6:39479 (11 pgs.) Dec. 2016).

Weaver el al., "Grover Disease (Transient Acanlholylic Dermatosis)," Arch Pathol Lab Med, 133:1490-1494 (Sep. ?? 009).

Skin Disorders in Older Adults: Papulosquamos and Bullous Diseases, Part 1. Published in: Consultant, vol. 51, issue B, dated Mar. 2011.

Phototherapy for neonatal jaundice, The Royal Children's Hospital Melbourne, Dec. 2018.

\* cited by examiner

DEVICE FOR PHOTO-THERAPY AND USE THEREOF

CROSS-REFERENCE TO RELATED APPLICATIONS

This application is a continuation-in-part of application Ser. No. 16/168,768 filed Oct. 23, 2018, which is a continuation-in-part of application Ser. No. 15/608,588 filed May 30, 2017, the entire content of which is expressly incorporated herein by reference thereto.

FIELD OF THE INVENTION

Embodiments of the present invention are directed to the field of phototherapy. Specifically, embodiments of the present invention are directed to methods and systems for providing phototherapy to treat internal conditions of patient.

BACKGROUND OF THE INVENTION

Blue wavelength photometric immune therapy provides a non-medicinal a non (drug free) method to bolster the immune systems of the elderly or of these with some form of dysfunctionality in their immune systems effectiveness. The human body fights off pathogens with cells that are produced in bone marrow called lymphocytes. Some of these lymphocytes enter the blood stream (B-cells). The majority (~75%) enter the lymphatic system, largely housed in the thymus gland and are vital to protect the body from infection.

These white blood cells are called T-cells of which there are 3 types:
  Cytotoxic T-cells (killer T-cells)
  Helper T-cells (direct the immune response of both T & B cells)
  Regulatory T-cells (suppress the immune system to keep its responses in check—preventing auto immune disease)

T-cells are housed in the front two layers of skin. 1 million T-cells exist per $cm^2$ of the skins surface. Frequent exposure to the sun, such as occurs in the summer, has been found to stimulate the T-cells housed in the skin. In particular, the blue wavelength range of sun light (380-490 nm) has been found to increase T-cell motility by 300% and immune systems efficiency by 7 to 8-fold (Phan, T., Jaruga, B., Pingle, S. et al. Intrinsic Photosensitivity Enhances Motility of T Lymphocytes. Sci Rep 6, 39479 (2016)) https://doi.org/10.1038/srep39479. In contrast, in winter when exposure to sun is minimal diseases proliferate.

In some conditions, photo-therapy may be effective to treat some conditions such as Grover's disease, including exposing the skin to controlled amounts of natural sunlight, ultraviolet A light (UVA, wavelength of 315-400 nm), or ultraviolet B light (UVB, wavelength of 280-315 nm). Unfortunately, exposure to light can sometimes intensify Grover's disease. Medium-dose UVA cold-light monophoto-therapy containing a special filtering and cooling system has been tested for administration to treat Grover's disease. It did result in some improved skin status and was well-tolerated without the occurrence of acute side-effects. (Breuckmann et al., Medium-dose ultraviolet A1 phototherapy in transient acantholytic dermatosis (Grover's disease), J. Am Acad Dermatol, January 2005, vol 52, no 1, pages 169-170).

Various devices have been designed to provide photo-therapy for a variety of skin treatments or tanning. U.S. Pat. No. 6,896,693 (Sullivan, Photo-therapy Device) discloses a photo-therapy device containing arrays of light-emitting diodes (LED) allowing the therapeutic treatment to take place at a more comfortable distance from the patient's skin surface, including whole body treatment. U.S. Pat. No. 7,066,941 (Perricone, Apparatus for skin treatment) discloses a system comprising an array of LEDs having a wavelength of about 400-500 nm for treating aging or damaged skin. US 2012/0101557 A1 (Wagenaar Cacciola et al., Treatment apparatus and use thereof for treating psoriasis) discloses an apparatus comprising a radiation source emitting radiation and a radiator for guiding the emitted radiation to the parts of the skin which is affected by psoriasis. EP 2044943 A1 discloses a photo-therapy device comprising a matrix board with LED (red light and blue light wavelength) and a control system board for preventive treatment, rehabilitation and the treatment of many diseases. US 2008/0065056 A1 (Powell et al., Skin treatment photo-therapy method) discloses a photo-therapy device with the design of a clamshell structure, pen shape, facial mask, or desk lamp comprising multi-color LEDs for emitting multiple wavelengths of light for treating skin conditions, including acne, wrinkle, rosacea, sun spots, inflammation, lesions, or skin blemishes. U.S. Pat. No. 9,463,333 B2 (Wagenaar Cacciola et al., Skin treatment device, lamp and use) discloses a device comprising lamps emitting UV-light and blue light (400-440 nm) for tanning and anti-acne.

US patent application no. 2006/0293727 A1 discloses a system and method comprising a plurality of light emitting diodes for treating an exposed tissue of a patient with a light energy, wherein the light emitting diodes are disposed over an area of a supporting structure. US 2006/0293727 A1 does not disclose the use of blue LED light but instead discloses the use of light energy comprising a substantial band of wavelengths between about 380 and 800 nm which wavelengths cover the full spectrum of visible light. US 2006/0293727 A1 discloses an LED fixture and detailed design parameters for treating acne using low power, broader range of light wavelengths to fluoresce small, specific skin surface areas. Fluoresce requires utilizing light on a specific tissue area to fluoresce active bacterial molecules of the exposed tissue, meaning to give off electrons in the tissue cells which causes the cells to die.

It is desired to provide methods and systems for replicating the sun's positive (blue light) effect on the body to address immune system dysfunction and weaknesses. It further desired to treat a variety of health conditions and diseases by irradiating the patient with specific amounts of light having specific ranges of intensity and wavelength thereby stimulating the immune system.

SUMMARY OF THE INVENTION

Embodiments of the present invention teach methods and devices for treating medical conditions using photo-therapy. In some embodiments, the present invention provides a photo-therapy device and use thereof for preferably treating Grover's disease, also known as transient acantholytic dermatosis, and other diseases which are associated or co-existed with Grover's disease. In some embodiments, the medical conditions also include internal medical conditions affected by a patient's immune system response involving T cells. For example, these medical conditions include, but are not limited to, autoimmune diseases (e.g., type 1 diabetes, Addison disease, rheumatoid arthritis, multiple sclerosis, celiac disease, systematic lupus, Crohn's disease and chronic inflammatory demyolinating polyneurapathy (CIDP)), cancer tumors mediated by active T cells, lung infection (e.g., such as Corona virus infection and pneumonia), HIV, and upper respiratory infection (e.g., bronchitis and sinus infections). The skin exposure of blue light at appropriate dosages can potentially eliminate or reduce Grover's dermatitis. The present invention provides a phototherapy device to treat Grover's disease through skin exposure of blue LED light to stimulate the body's immune system to reduce itch, blotchiness and discomfort of skin. Alternatively, for the same effect, blue fluorescence light can be applied to skin.

In the present invention, the term "substantially uniform radiation" is used to mean radiation of an amount and direction such that all portions of the exposed skin of the subject's body are exposed with radiation at a distance that provides an intensity to meet the minimum requirements for treatment. It is recognized that the radiation can be applied from blue LED light emitting lamps arranged to uniformly radiate one side (i.e., the front) of the subject while the subject is lying on a bed or table, before the subject can turn over so that his or her back side can be exposed to the radiation (or vice versa). In other embodiments, a vertical surface with such lamps can be provided for sequential front and back (or back and then front) exposure, or a round or pentagonal chamber can be provided with lamps that are arranged to provide simultaneous radiation around and surrounding the subject.

Grover's disease is a transient, self-limiting, and non-immune-mediated skin disorder that consists of papulovesicular rash. The rash is frequently triggered or aggravated by heat, sweating, ultraviolet light exposure, or hospitalization. Grover's disease and other associated dermatitis worsen in winter season. The acantholysis seen in Grover's disease occurs in a variety of different patterns singly or in combination characterized by four different acantholytic histologic patterns, resembling Darier-White disease, pemphigus vulgaris, pemphigus foliaceous, Hailey-Hailey disease, and a spongiotic dermatitis. Grover's disease has been found to be associated with numerous disorders, including hematologic malignancies and occasionally coexisted with other dermatoses including asteatotic eczema, allergic contact dermatitis, atopic dermatitis, irritant contact dermatitis, and psoriasis. (Weaver et al.)

The pathogenesis or the cause of the manifestations of Grover's disease is unknown, but it could relate to the occlusion of damaged eccrine ducts with sweat dispersion in the upper layers of the skin due to its association with sun exposure, heat, sweating, trauma, or sun damaged skin. Grover disease may be considered as a syndrome representing a host inflammatory response to disseminated lesions rather than as a distinct disease. (Weaver et al.) Its nature of spontaneous remittance and occasional fluctuant course with unknown pathogenesis makes the evaluation of treatment difficult and challenging.

Sunlight exposure is both harmful and beneficial to the physiology of human skin. Despites a causative link in skin cancers relevant to ultraviolet (UV) light exposure, sunlight is also associated with positive health outcomes including reduced incidences of autoimmune diseases and cancers. The effects of sunlight in immune function remain unclear. Visible radiation (400-750 nm) penetrates much deeper into the dermis of the skin than UV light.

Human keratinocytes and skin-derived endothelial cells were radiated with LED devices of distinct wavelengths to study the effects on cell physiology. Blue light may be effective in treating hyper-proliferative skin conditions by reducing proliferation by inducing differentiation in human skin-derived keratinocytes. LED radiation with blue light at high fluences, however, can be toxic for endothelial cells and keratinocytes. (Liebmann et al., Blue-light radiation regulates proliferation and differentiation in human skin cells, Journal of Investigative Dermatology, 2010 January; 130 (1):259-69)

Blue LED light of the wavelengths disclosed herein is capable of penetrating several millimeters through skin. Studies have been done to show that the low doses of blue or full spectrum light were not toxic to T lymphocytes, a cell-type highly abundant in skin performing immune surveillance, including memory cells that can be activated in the skin by antigen-presenting cells and other cells actively recruited by inflammation. T lymphocytes had the capacity to sense and respond to light. Blue light stimulated the production of $H_2O_2$ in T lymphocytes in vitro. $H_2O_2$ activated a kinase/phospholipase signaling pathway and $Ca^{2+}$ mobilization. The intrinsic photosensitivity of T lymphocytes may enhance their motility in skin, which may contribute to the effects of sunlight on immune function. (Phan et al., Intrinsic photosensitivity enhances motility of T lymphocytes, Scientific Reports, 2016 Dec. 20; 6:39479).

The blue light exposure that is applied according to the present invention covers the entire exposed surface area of the subject's skin including both the front and back of the subject's body in order to induce massive T cell activation. This is achieved using high output LED blue lights preferably applied to the entire exposed skin surfaces of the subject's body to obtain an effective treatment. The amount of radiation applied to the subject ranges from at least about 250 to as much as about 3000 Watts-minute or more, preferably at least about 600 Watts-minute and more preferably at least about 1200 Watts-minute. The radiation energy that is actually to be absorbed will depend upon the patient's size physiology and degree of rash intensity, but these values have been proven to be optimum for various sized patients. Absorption also depends upon the lamp wattage and time of treatment. The subject to be treated is typically a male patient that is 40 years old or older as that is when the Grover's disease is typically encountered for such subjects. Although there is no upper age limit, such treatments are usually applied to male patients that are between 40 and 90.

Blue LED light radiation is provided for use in treating skin rash on exposed skin surfaces of at least a subject's upper torso including both front and back sides so that the subject is exposed to between about 250 and 3000 watt-min watts-minute of such radiation, wherein the radiation is uniformly applied to the exposed skin surfaces by a plurality of blue LED light generating lamps each having a wattage of at least 15 W or more and at a total exposure time of at least about 10 minutes or more per each of the both front and back sides, with the emitted blue light having a wavelength in the range of between about 400 and 490 nm. There is no upper limit on the wattage of the lamps except to the extent that such lamps are not available, commercially or otherwise. Blue LED lamps having a wattage of about 175 to 210 W have been made and used and these lamps include a cooling mechanism or heat sink to avoid excessive temperatures. In particular, for initial testing of the invention, two blue LED light sources have been used with each having the following performance factors: 210 Watts, Radiant power of 105 watts at 450 nm wavelength. The wavelength distribution is tight with 99% at 450 nm. Beam pattern is Lambertain on a 22 inch (0.56 m) long light source emitting surface. The power source or driver is 120 volt input with 240 Volts AC 50/60 Hz. and is self-grounded. Of course, other lamps with lower or higher wattage can be used provided that they generate blue light. The blue LED lamps can be provided as any type of bulb, including Reflector and Par lamp configurations as well as tube lamps or baton lamps provided that it possesses the necessary wattage described herein. Some of these lamps are non-conventional but lamp suppliers are able to prepare custom devices having the necessary performance requirements upon request.

Additional testing of the present invention was conducted using 35-40 watt baton lamps. These LED baton lamps are preferred for use in the photo-therapy devices of the present invention to provide more uniform light coverage and the desired radiation. The LED baton lamp has a typical wattage in the range of about 25 to 60 watts, preferably about 35 to 50 watts, and emits light in wavelength range of from about 400 to 490 nm or from about 410 to 490 nm, preferably with the center of the spectrum at 450 nm. The LED baton lamp has the length in the range of about 1.5 to 2.5 feet (0.457 to 0.762 m), preferably in the length of about 58.42 cm (23 inches). The effectiveness of the LED photo-therapy device is enhanced when the LED baton lamps operate in high output levels and are configured to apply the blue light as uniformly as possible. In appearance, they provide blue light in a manner reminiscent of a fluorescent bulb except that the light is blue and stronger in intensity. In the case of using a fluorescent bulb, embodiments of the present invention was conducted using, for example, a blue-light radiating device comprising seven 1.5 feet continuous wave fluorescent batons. Each of the fluorescent baton has a typical wattage in the range of about 32 watts (total 224 watts).

The wattage of the lamps is not critical but the larger the wattage, the shorter the time of treatment. While between about 5 Watts and 100 Watts are suitable, the exposure times at 5 watts is relatively long while making 100 Watt lamps would be relatively expensive. In some embodiments, at least 15 Watts are desirable. Accordingly, the wattage in the range of about 25 to 60 watts, preferably about 35 to 50 watts, are the best ranges as these can be made more easily and less expensively while also providing relatively shorter times for the subject to be exposed to the necessary amount of radiation for successful treatment. As noted herein, single or repeated treatment times of between 30 and 40 minutes at the preferred wattages is generally effective.

The absorption of the radiation can be calculated. As a matter of clarification, absorption of the radiation is in reference to the energy hitting the subject's body at the surface. First of all, while the total skin area of a person is around 2.1 m$^2$, this include portions of the skin that do not usually receive light, e.g., underarms and armpits, etc. Calculations have been made that demonstrate that the exposed skin area of a subject can vary from about 1.2 to 1.56 m$^2$. For an average application of blue LED light from lamps having a wattage of between 35 and 40 watts applied at a distance of 15.25 cm (6 inches) from the subject's skin (see Table 1), 31.8 watts/m$^2$ are absorbed. Thus, the amount of radiation absorbed by the subject's exposed skin surfaces during three treatments of 16 minutes each would be calculated as follows:

31.8 watts/$m^2$×16 min×3 treatments (for each side)× 1.2 $m^2$=1831.68 watt-min.

For the larger surface area of 1.56 m$^2$, the calculation is:

31.8 watts/$m^2$×16 min×3 treatments (for each side)× 1.56 $m^2$=2381.18 watt-min.

Accordingly, variations in distance, wattage, surface area and the like can vary the absorbed blue light energy over the ranges disclosed in this specification.

Each photo-therapy device may comprise between 2 and 12 but preferably one to four LED baton lamps or two or four LED baton lamps in each device depending upon the type of exposure. The LED baton lamps can be mounted to a wall to minimize the occupied space of the device to minimize the use of tight office space found in most dermatologist offices. The LED baton lamp can be affixed to a movable surface to provide a portable device. Each lamp can be provided upon a separate support that is movable to provide the greatest flexibility of moving the lamps into the best positions for applying the radiation to the subject. For simplicity, the lamps can be provided on a single support that is pivotally mounted on a wall or pillar so that it can be moved away to allow the subject to be placed in the correct position before then being moved toward the subject and at the best distance for providing absorption of the blue light. Therefore, the photo-therapy device of the present invention provides a convenient solution and advantages as a portable or/and compact photo-therapy device which has minimal occupied space or can be in storage or hidden away.

Embodiments of the present invention also disclose a method for treating a medical condition in a patient in need thereof. The method includes applying light to the patient thereby stimulating the immune system of the patient, wherein the applying includes irradiating substantially the entire body of the patient with high intensity blue light having a wavelength, intensity, and duration configured to provide immune system stimulation sufficient to treat the medical condition, the stimulation including increasing the population of T-cells in the patient's bloodstream to treat the medical condition.

In some embodiments, the medical condition includes an infection and the stimulation of the immune system includes increasing the motility of T-cells housed in the skin to treat the infection.

In certain embodiments, the medical condition includes an internal condition and the stimulating includes stimulating and increasing the delivery of T-cells to internal organs.

In some embodiments, the medical conditions also include internal medicine conditions affected by a patient's immune system response involving T cells. For example, the medical conditions include, but are not limited to, autoimmune diseases (e.g., type 1 diabetes, Addison disease, rheumatoid arthritis, multiple sclerosis, celiac disease, systematic lupus, Crohn's disease and chronic inflammatory demyolinating polyneurapathy (CIDP)), cancer tumors mediated by active T cells, lung infection (e.g., such as Corona virus infection and pneumonia), HIV, upper respiratory infection (e.g., bronchitis and sinus infections) or a combination thereof.

In certain embodiments, the applying light to the patient includes irradiating the patient with blue light having a wattage of about 210 Watts, a wavelength between about 400 and 490 nm or between about 410 and 490 nm, and an irradiance or intensity of about from about 70 watts/m$^2$ to about 140 watts/m$^2$ for a total duration of about 20 minutes.

In some embodiments, the applying light to the patient includes irradiating the patient with an intensity, a duration, or a pattern blue light based on the weight, height, or sex of the patient.

In certain embodiments, the applying light to the patient includes alternating period of irradiation times and rest times.

In some embodiments, the applying light to the patient includes monitoring the amount of light received by the patient and dynamically adjusting an intensity or irradiation pattern of the light to match a target amount of received light.

In certain embodiments, the applying light to the patient includes irradiating the patient with an amount of blue light equivalent to 4 to 6 hours of summer sunlight.

Embodiments of the present invention also disclose a method for treating an internal medical condition in a patient in need thereof. The method includes applying light to the patient thereby stimulating the immune system of the patient, wherein the applying includes irradiating the patient with high intensity blue light having a wavelength between about 400 and 490 nm or between about 410 and 490 nm and an irradiance or intensity of about from about 70 watts/m$^2$ to about 140 watts/m$^2$ configured to activate and release T-cells housed in the skin into the patient's bloodstream to treat the condition.

Embodiments of the present invention also disclose a method for providing phototherapy to a patient. The method includes determining a target irradiance absorption and an irradiation pattern based on patient parameters including the sex, height, and weight of the patient; irradiating the patient with blue light having about 210 W of wattage according to the determined irradiation pattern; and monitoring an irradiation level of the patient during treatment, wherein the irradiance level is varied during treatment based on the monitored irradiation level to maintain the target irradiance.

In some embodiments, irradiating the patient includes illuminating the patient with a plurality of baton lamps configured to emit blue light having a wavelength between about 400 and 490 nm or between about 410 and 490 nm, the baton lamps being oriented longitudinally along the height of the patient with at least one baton lamp aligned with the patient's torso and another baton lamp aligned with the patient's legs.

In certain embodiments, each baton lamp is an LED lamp including a plurality of about 5 W LEDs, the baton lamp measuring about 24 inches long and 5½ inches wide.

In some embodiments, the method further includes cooling the baton lamps using cooling fins configured to dissipate heat, the cooling fins being disposed along the length of the baton lamps.

In certain embodiments, the irradiation pattern includes alternating periods of irradiation times and rest times.

In some embodiments, the patient parameters further include the posture of the patient, the posture including whether the patient is standing or sitting.

In certain embodiments, irradiating the patient includes installing the patient in an enclosure having a reflective internal surface configured to provide uniform illumination of the patient.

In some embodiments, monitoring the irradiation level of the patient includes installing a plurality of light sensors configured to measure light on the patient and receiving light level measurements from each of the plurality of sensors.

In certain embodiments, monitoring the irradiation level of the patient further includes displaying readings from the plurality of sensors on a controller configured to control illumination of the subject.

In some embodiments, the target irradiance is about from about 70 watts/m$^2$ to about 140 watts/m$^2$.

In certain embodiments, the irradiation pattern is calculated to provide the subject with the equivalent of blue light absorbed in 4-6 hours of summer sunlight.

Embodiments of the present invention also disclose a method of providing photo-therapy including illuminating a patient with blue light using a pair of baton lamps each having a wattage of between about 190 W and 230 W, the lamps being configured and arranged on one or more supporting inner surfaces of an enclosure surrounding the patient to provide a uniform application of the radiation onto exposed skin surfaces of the patient; wherein the baton lamps have a wavelength in the range of between 425 and 475 nm, and are oriented longitudinally along the height of the subject with at least two baton lamps aligned with the subject's upper torso and with at least two baton lamps aligned with the subject's legs with the lamps arranged about 7.62 cm to 30.48 cm (3 to 12 inches) from the subject's skin. In some embodiments, there are total seven baton lamps.

Embodiments of the present invention further disclose a device for providing phototherapy to a subject. The device includes a plurality of high-powered light sources configured to emit blue light having a wavelength between about 400 and 490 nm or between about 410 and 490 nm; a plurality of light sensors configured to be installed on the subject to measure an intensity of light; a controller coupled to the plurality of light sources and the plurality of light sensors and configured to control operation of the light sources, and an enclosure configured to house the subject during treatment; wherein the controller is further configured to determine and adjust an irradiation pattern based on patient information and the light sources irradiate the subject with the blue light based on the irradiation pattern to boost the subject's immune system. In some embodiments, the light sources are baton lamps. In certain embodiments, the phototherapy device includes at least two baton lamps oriented longitudinally along the height of the subject with at least one baton lamp aligned with the subject's torso and another baton lamp aligned with the subject's legs. In some embodiments, the photo-therapy device comprises between 2 and 12, or between 2 and 8, or between 2 and 4 light sources. In certain embodiments, the light sources provide a uniform application of the radiation onto exposed skin surfaces of the subject. In some embodiments, the light sources each have a wattage of about 25 to 60 watts or about 35 to 50 watts and at a total exposure time of about 15 to 100 minutes or about 25 to 50 minutes, with the emitted blue light having a wavelength in the range of between 400 and 490 nm. In certain embodiments, the lamps each have a wattage of about 175 to 210 watts and at a total exposure time of about 20 minutes. In some embodiments, the light sources are configured to be placed at about 3 to 12 inches away from the subject's skin. In certain embodiments, at least 600 watts-minute or at least 1200 watts-minute of such radiation is applied to the subject. In some embodiments, about 2500 watts-minute or between about 1000 and 4000 watts-minute of the blue LED light radiation is applied to the subject. In certain embodiments, the light sources are LED lamps or fluorescent lamps. In some embodiments, a pair of sensors is mounted on each of an upper chest, lower chest, stomach, and mid-thigh of the subject. In certain embodiments, the controller is configured to enable an operator to set target irradiation value, treatment time or relevant parameters for the treatment based on the subject's needs. Some embodiments are directed to an enclosure comprising the photo-therapy device. In certain embodiments, the photo-therapy device comprises two of the high-powered light sources that are aligned vertically from each other. Optionally, the light sources are mounted in uniformly spaced locations on the internal surface of the enclosure. Optionally, the enclosure comprises a door.

In certain embodiments, the light sources are LED lamps having a wattage of about 210 Watts.

In some embodiments, each LED lamp includes a plurality of about 5 W LEDs.

In certain embodiments, the LED lamps are about 24 inches long and 5½ inches wide.

In some embodiments, the light sources include cooling fins configured to dissipate heat emitted by the light sources.

In certain embodiments, the controller is configured to enable a user to input the patient parameters including patient height, weight, and sex, and the controller is further configured to dynamically vary a light output of the light sources during treatment based on the patient parameters to maintain an irradiance value.

In some embodiments, an inner surface of the enclosure is lined with reflective material.

In some embodiments, the photo-therapy device includes a pair of baton lamps each having a wattage of between about 190 W and 230 W, the lamps being configured and arranged on one or more supporting inner surfaces of the enclosure to provide a uniform application of the radiation onto exposed skin surfaces of the patient; wherein the baton lamps have a wavelength in the range of between 425 and 475 nm, and are oriented longitudinally along the height of the subject with at least two baton lamps aligned with the subject's upper torso and with at least two baton lamps aligned with the subject's legs with the lamps arranged about 7.62 cm to 30.48 cm (3 to 12 inches) from the subject's skin.

Embodiments of the present invention further disclose a method for activating T cells in a subject in need thereof. The method comprises applying blue LED light radiation to exposed skin surfaces of the subject. The radiation is uniformly applied to the exposed skin surfaces of at least the subject's upper torso including both front and back sides by a plurality of blue LED light generating lamps each having a wattage of at least about 15 watts for a total exposure time of at least about 10 minutes per each of the both front and back sides. The emitted blue light has a wavelength in the range of between about 400 and 490 nm or between about 410 and 490 nm. At least about 250 watts-minute of the blue light radiation is applied to the subject. After applying the radiation, a serum concentration of a T cell marker increases in the subject. In some embodiments, the T cell marker is Interferon Gamma (IFN-γ). In some embodiments, the subject suffers from skin rash. The rash may be present on the subject suffering from Bullous pemphigoid, Lichen planus, porokeratosis, Grover's disease or diseases which are associated or co-existent with Grover's disease. In other embodiments, the subject suffers from an internal medicine condition. The condition may comprise autoimmune diseases, cancer tumors mediated by active T cells, lung infection, HIV, upper respiratory infection or a combination thereof. The autoimmune diseases may comprise type 1 diabetes, Addison disease, rheumatoid arthritis, multiple sclerosis, celiac disease, systematic lupus, Crohn's disease, chronic inflammatory demyolinating polyneurapathy (CIDP) or a combination thereof. The lung infection may comprise Corona virus infection, pneumonia or a combination thereof. The upper respiratory infection may comprise sinus, bronchitis, throat infections or a combination thereof.

The details of the preferred embodiments of the present invention are set forth in the accompanying figures and detailed description herein. Once these details of the invention are known, numerous additional innovations and changes will become obvious and implementable to one of ordinary skill in the art.

BRIEF DESCRIPTION OF THE FIGURES

Further features of the inventive concept, its nature and various advantages will be more apparent from the following detailed description, taken in conjunction with the accompanying figures:

FIG. 1 is a perspective schematic view of photo-therapy devices according to the invention, wherein FIG. 1A shows a two baton lamp upper torso exposure device while FIG. 1B shows a four baton lamp full body exposure device.

DETAILED DESCRIPTION OF THE INVENTION

Further in relation to this, before explaining at least the preferred embodiments of the invention in greater detail, it is to be understood that the invention is not limited in its application to the details of construction and to the arrangements of the components set forth in the following description. It would be understood by those of ordinary skill in the art that embodiments beyond those described herein are contemplated, and the embodiments can be practiced and carried out in a plurality of ways. Also, it is to be understood that the terminology used herein is for the purpose of description and should not be regarded as a limiting factor.

Unless otherwise defined, the terms used herein refer to that which the ordinary artisan would understand such term to mean based on the contextual use of such term herein. To the extent that the meaning of a term used herein as understood by the ordinary artisan based on the contextual use of such term differs in any way from any particular dictionary definition of such term, it is intended that the meaning of the term as understood by the ordinary artisan will prevail.

As used herein, the term "about" means approximately or nearly and in the context of a numerical value or range set forth, herein means±10% of the numerical value or range recited or claimed, and preferably ±5% of the same.

The term "treating" includes delaying, alleviating, mitigating, or reducing the intensity, progression, or worsening of one or more attendant symptoms of a disorder or condition and/or alleviating, mitigating, or impeding one or more causes of a disorder or condition. Treatment under the claimed invention may be a preventative treatment, prophylactic treatment, remission of treating or ameliorating treatment.

The term "therapeutically effective amount" or "therapeutically effective dose" refers to the amount of a composition, compound, light, radiation, energy, therapy, or course of treatment that, when administered to an individual for treating a disorder or disease, is sufficient to effect such treatment for the disorder or disease. The "therapeutically effective amount" will vary depending on the composition, the compound, the radiation, the energy, the therapy, the course of treatment, the disorder or disease, and its severity, and the age, weight, etc., of the individual to be treated.

Throughout this description, the preferred embodiments and examples provided herein should be considered as exemplar, rather than as limitations of the present invention.

Figures 1A, 1B:
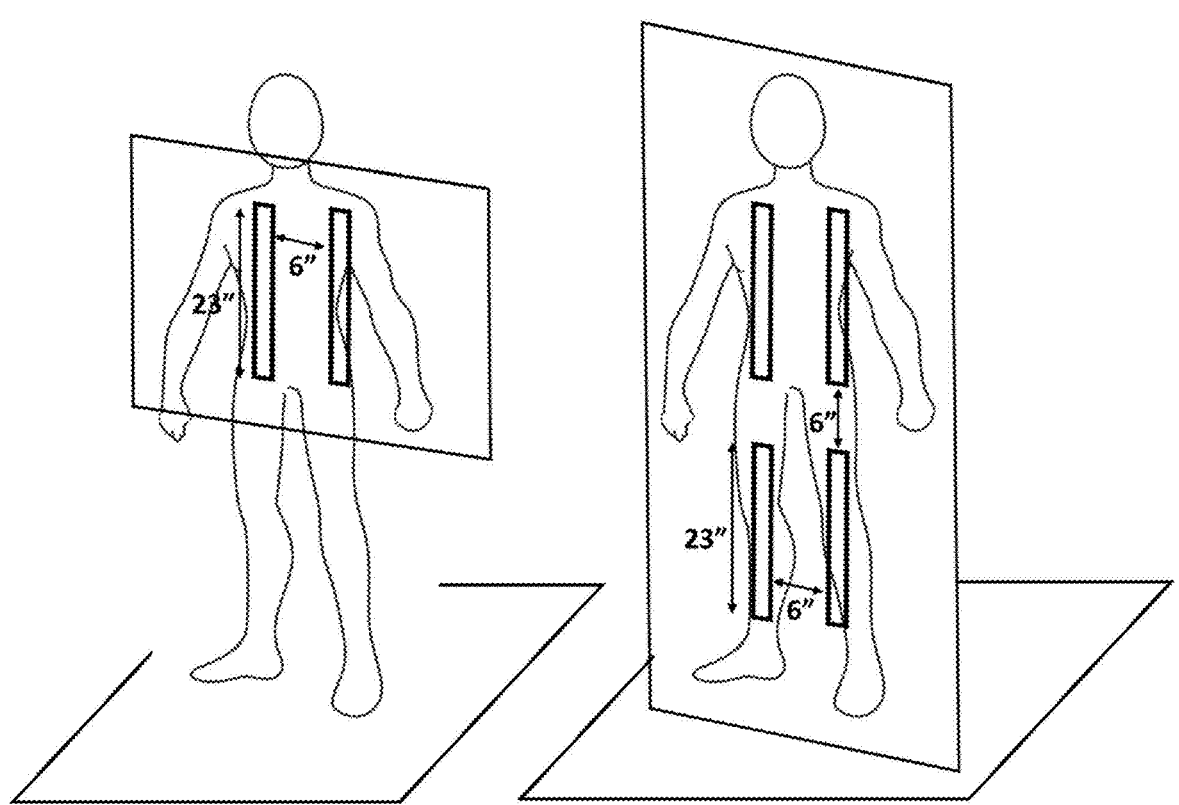

In one embodiment, the photo-therapy device of the present invention comprises four LED baton lamps which are mounted to a wall as shown in FIG. 1B. Preferably, the distance between two vertical lamps in parallel is about 15.24 cm (6 inches), and the distance between the upper and lower lamps is about 15.24 cm (6 inches) as shown in FIG. 2B. The arrangement in FIG. 1B provides exposure of the entire body one side at a time. When the skin rash occurring from Bullous pemphigoid, Lichen planus, porokeratosis, Grover's disease or diseases which are associated or co-existent with Grover's disease is mostly in the upper trunk of the body, the photo-therapy device of FIG. 1A can be used, as it is smaller and simply comprises two LED baton lamps mounted to a wall or a movable surface to provide a more compact photo-therapy device. The embodiment of the photo-therapy device shown in FIG. 1A provides LED blue light exposure of only the upper trunk or torso of the subject, while in FIG. 1B the exposure is of the patient's full body. The full body exposure is preferred because it provides maximum absorption at a minimum time, but for cases of lesser severity, the upper torso exposure is sufficient. The full body exposure is also preferred because it provides the greatest increase in T cells in the body which would fight the infection.

In an embodiment, a patient stands in front of the light source to expose the front side of the body and then turns around to expose the back side of the body to the light source. The skin of the patient with Grover's disease is exposed to the LED light radiation, but eyes of the patient are protected from the LED lights, such as wearing dark sunglasses with heavy tint or non-transparent material, or by a blindfold that is capable of shielding the subject's eyes from the light. Additionally, the lamps may be typically mounted on a structure or structures that do not extend above the neck of the patient to minimize the light being directed at the patient's face and eyes. Alternatively, the lamps may cover the head and face, in which case the patient can wear blackout glasses or goggles to protect the eyes.

Figure 2:
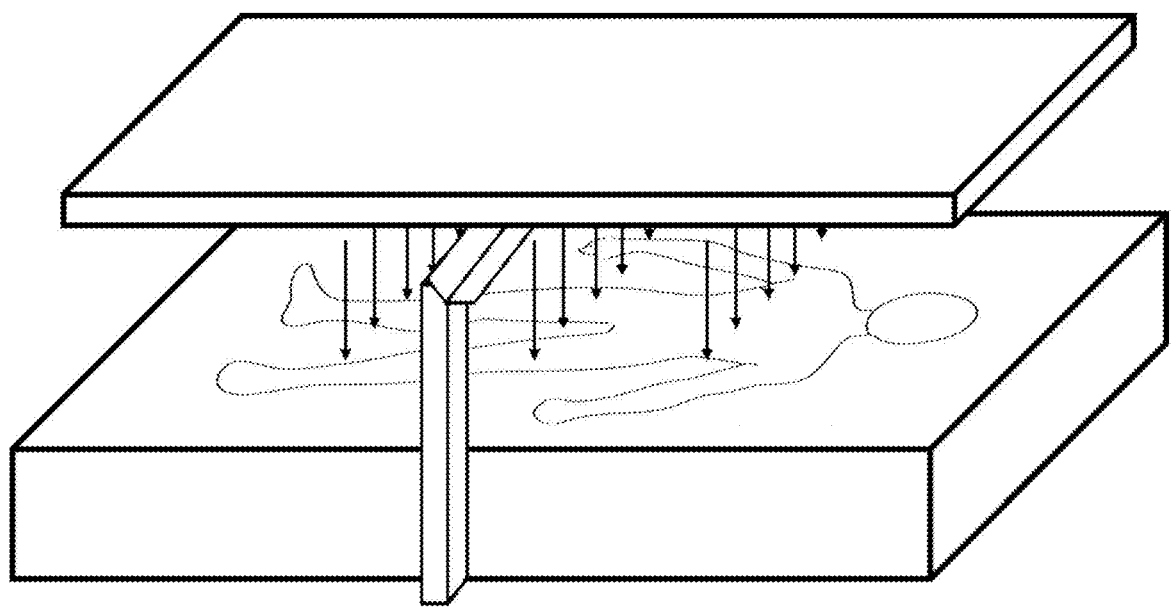
FIG. 2 shows the horizontal operation mode of a photo-therapy device for a patient laying on a bed, wherein a hinge is attached to the long edge of the photo-therapy device.
Figure 3:
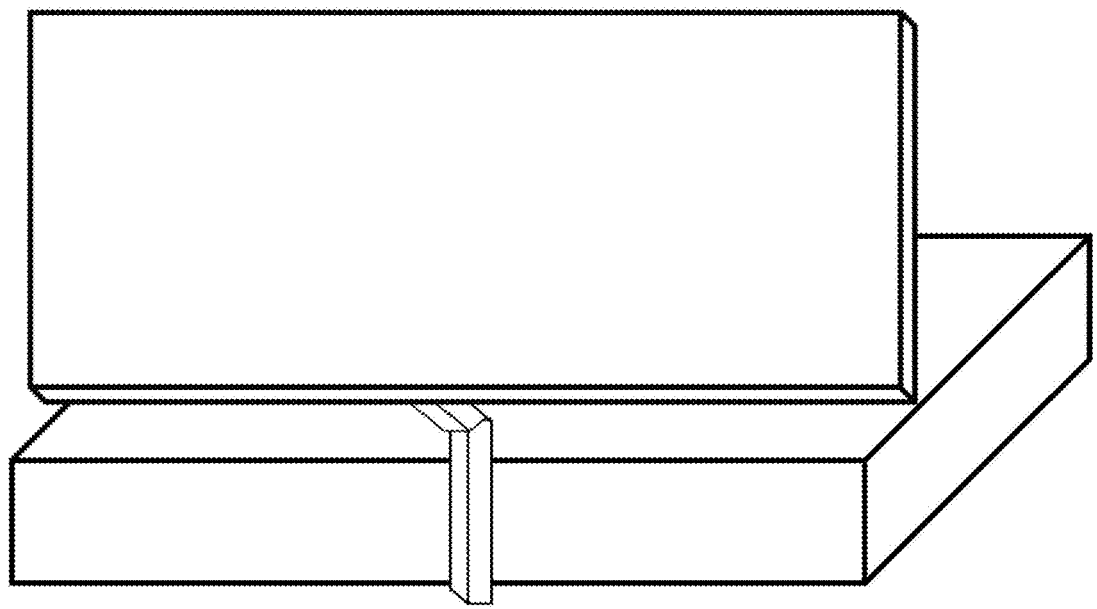
FIG. 3 shows a photo-therapy device in an upright position, wherein a hinge is attached to the long edge of the photo-therapy device.
Figure 4:
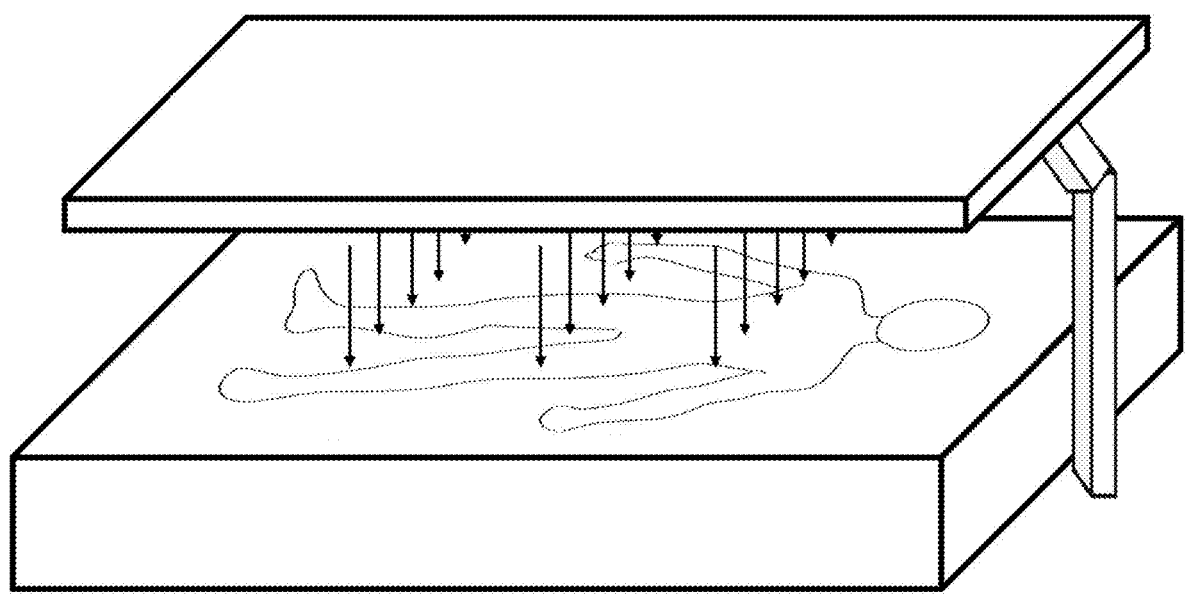
FIG. 4 shows the horizontal operation mode of the photo-therapy device for a patient laying on a bed, wherein a hinge is attached to the short edge of the photo-therapy device.
Figure 5:
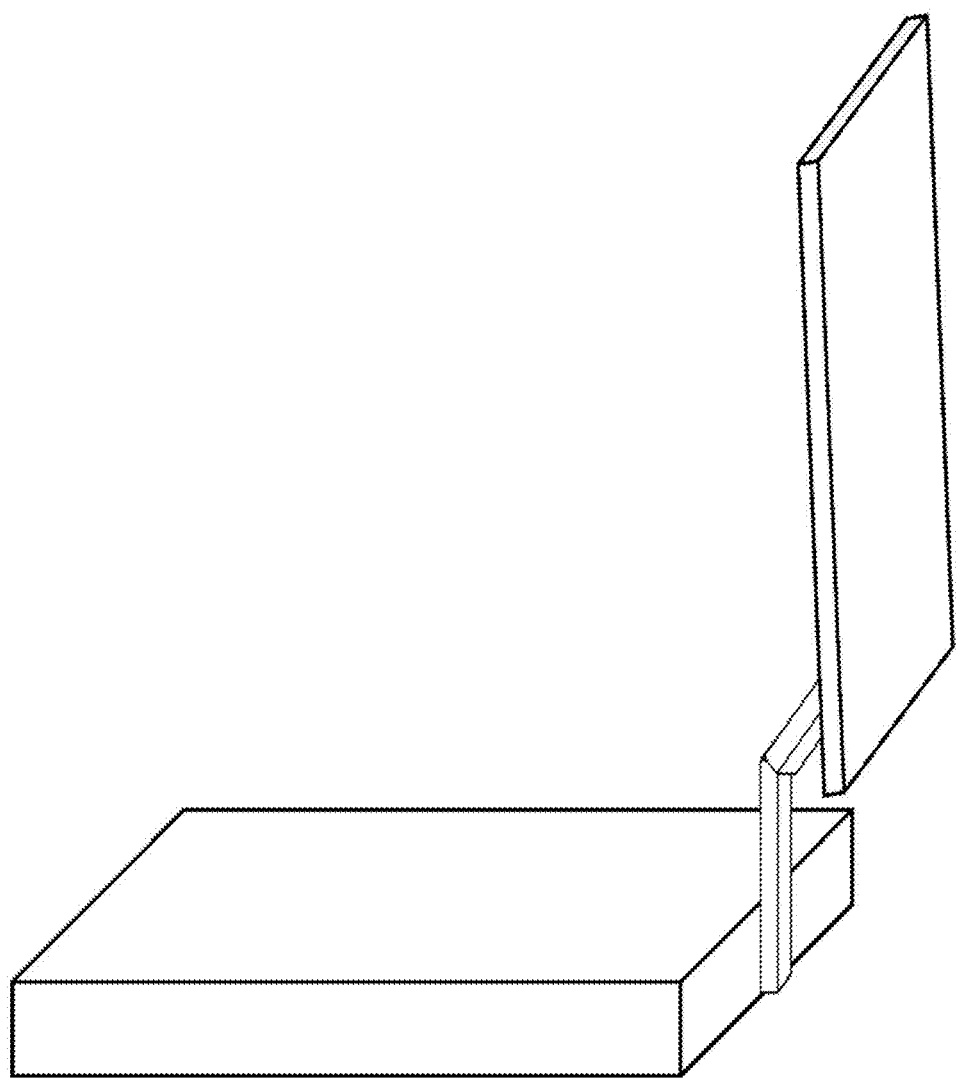
FIG. 5 shows a photo-therapy device in an upright position, wherein a hinge is attached to the short edge of the photo-therapy device.

In another embodiment, the LED baton lamps are affixed to a movable surface, wherein a hinge is attached to the movable surface as shown in FIGS. 2-5. The hinge or pivot point can be attached to the short or long edge of the movable surface depending on the mode of operation or the layout of the doctor's office. The hinge may comprise multiple components to support different positions of the movable surface and may be mounted to a wall or a floor. In one embodiment, a patient lays on a bed, and a photo-therapy device is positioned above the patient's body to provide light exposure as shown in FIGS. 2 and 4. When the photo-therapy device is not in use, it can be positioned in upright position against the wall to minimize the occupied space of the photo-therapy device as shown in FIGS. 3 and 5.

And instead of being mounted on a support, the photo-therapy device can be attached to a wall with a connection that allows the support surface to be pivoted to be adjacent a table or a bed for exposure to the person when the person is lying down.

In yet another embodiment, the lamps can be mounted in a circular or oval chamber which surrounds a standing patient. Part of the chamber acts as a door to allow the subject to step inside before energizing the lamps. Although some subjects may not be comfortable standing in a relatively snug chamber, this embodiment provides maximum radiation exposure and minimum treatment times.

In additional embodiments, the light sources can be made into or incorporated in a blanket or other structure which is configured to surround the patient so that all sides of the patient's body are treated simultaneously. The lamps can be spaced on the blanket or interior surface of the structure to facilitate directing the blue LED light at all body surfaces. The structure can be a polygonal, oval or cylindrical chamber or enclosure that is either closed or open at the top. Preferably, the enclosure does not extend above the head of the person to be treated to minimize concerns of eye damage from light exposure. Alternatively, the lamps can be positioned only adjacent the patient's upper torso and legs as shown in other embodiments herein. The wattage and treatment time would be the same as in the other embodiments disclosed herein.

Figure 7:
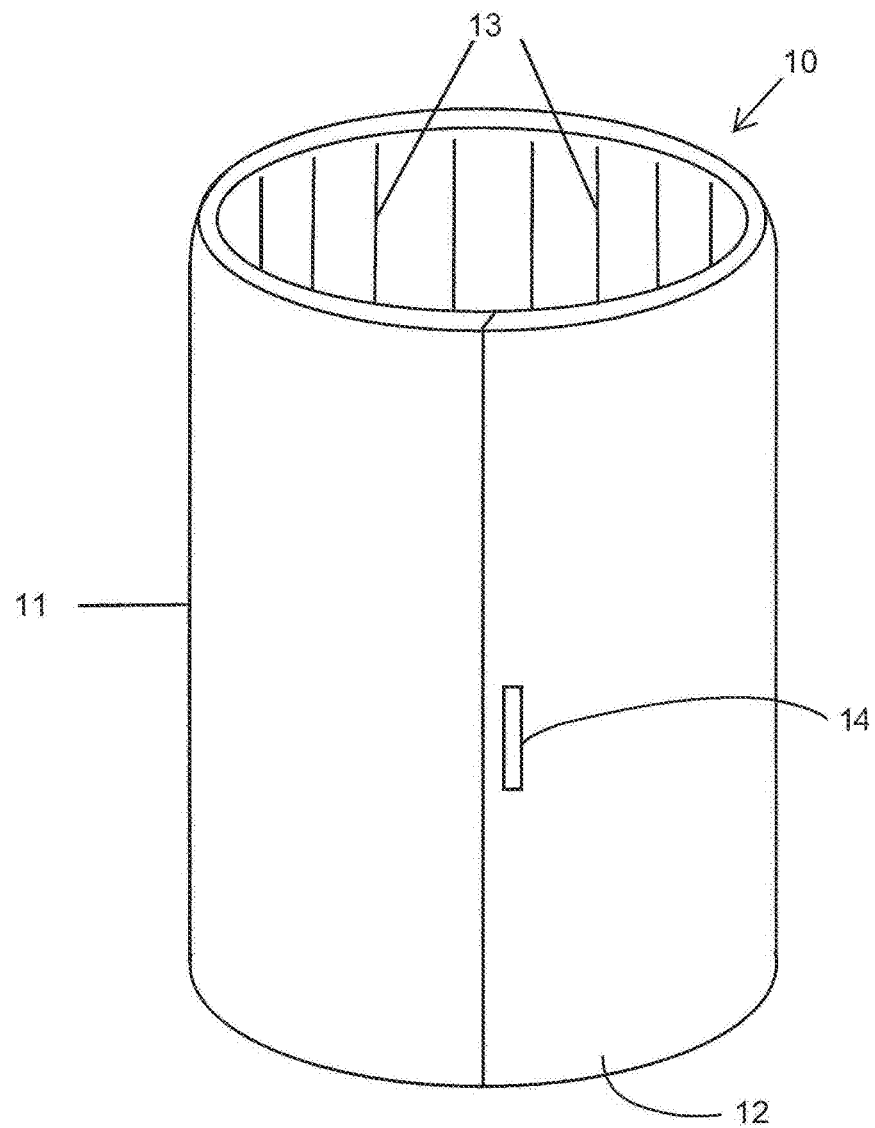
FIG. 7 illustrates a cylindrical chamber for surrounding the patient and directing blue LED light at all skin surfaces.

As shown in FIG. 7, a cylindrical enclosure may be provided. This enclosure can include a door or movable panel that would allow the patient to enter into the enclosure. The LED lamps would be mounted in uniformly spaced locations on the internal surface of the enclosure so that the patient's entire body is illuminated with the blue LED light. In a preferred embodiment, the enclosure is not taller than the height of the person who is being treated. Typically, a height of about 5 feet is acceptable, with a small raised platform being placed inside of the enclosure for shorter people so that their head extends above the top surface of the enclosure. Alternatively, the enclosure can be configured to be raised or lowered to conform to the height of the individual patient to be treated.

The cylindrical enclosure or chamber 10 of FIG. 7 includes a wall member 11 that provides the enclosure, access to which is provided by door 12 which is openable by handle 14. As noted herein, a square rectangular or other polygonal shaped enclosure can also be used. The lamps 13 can be mounted on the interior surface of the chamber so that when illuminated all body surfaces of the patient standing therein would be exposed to the blue LED light radiation.

In some embodiments, the door can instead be a sliding door or a curtain. For these, the door or curtain would not include lamps so the patient would have to change position during the treatment to obtain uniform coverage of the LED light on his or her body.

When a blanket enclosure is used, it can be suspended from hoops or mounted on a structure that provides the blanket in a vertical orientation in a configuration that surrounds the patient.

Figure 6:
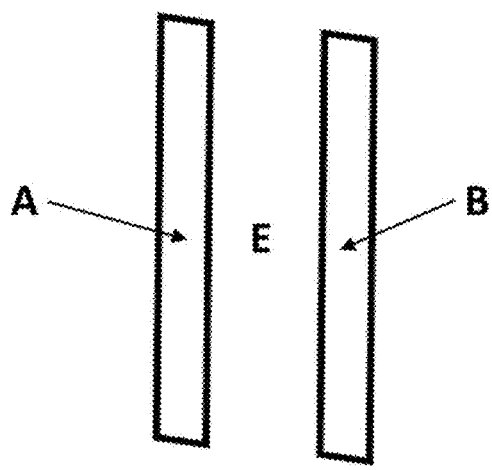
FIG. 6 shows different location points which are identified for radiation measurement. The identified location points (A, B, C, D, E and F) are labeled in relevance to the positions of the LED baton lamps.
Figure 6:
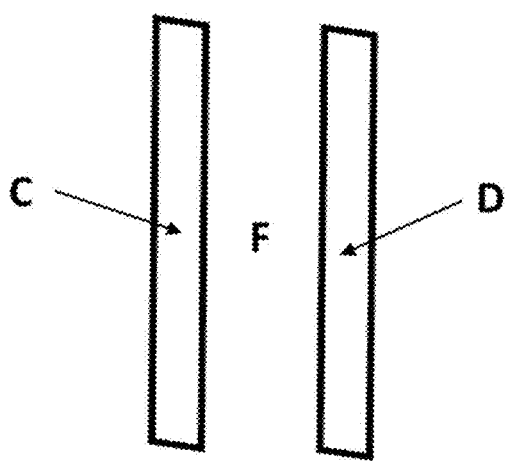

For all embodiments, the exposed skin can be at the distance of about 7.62 cm to 30.48 cm (3 to 12 inches), preferably at the distance of about 10.16 cm (4 inches), or preferably at the distance of 30.48 cm (10 inches) from the LED light source. When the distance from the LED light source is at least about 25.4 cm (10 inches), the radiation measurements for different locations (i.e. locations A, B, C, D, E and F as shown in FIG. 6) reach similar levels with equal exposure.

The skin in back and front sides of the body is exposed to the LED light source in equal length of time for each treatment. In one embodiment, the total exposure time for both the front and the back sides of the body is about 15 to 100 minutes, preferably about 25 to 50 minutes (in single or multiple treatment sessions, as the absorbance is cumulative. In the most preferred embodiment, the radiation is provided in the range of about 1200 to 2000 watt minutes at about 30 to 50 watts for treatment times of about 25 to 50 minutes.

The exposure of the LED light through the photo-therapy device and the method of use thereof of the present invention provides effective treatment of the Grover's disease by delivering sufficient energy in blue light for absorption by the exposed skin surfaces of the subject to improve the condition of the rash. These improvements are obtained without the use of pharmaceutical agents applied by ointments, creams or lotions after the light exposure.

Treatment for Internal Conditions

Embodiment of the present invention further provide methods and systems for treating internal conditions. The methods and systems that follow constitute variations and improvements of the above-described methods and systems for the treatment of skin conditions. In particular, embodiments of the present invention disclose a method for treating a medical condition in a patient using blue light. The method includes irradiating the patient with blue light having a wavelength, intensity, and duration that provides immune system stimulation sufficient to treat an internal medical condition such as an infection. In particular, therapeutically effective amounts of blue light have been found to boost the immune system of a patient by stimulating the release of T-cells housed in the skin to fight internal conditions such as infections or other conditions that may involve the skin or other surface areas of the body but are not limited to it.

Embodiment of the present invention thus provide methods and systems of providing phototherapy to a subject. Specifically, embodiments, of the present invention provide a methods and systems for delivering specific amounts of blue light treatment to a subject to stimulate the immune system. The invention is generally suited for subjects whose immune response is less than optimal or whose immune system is otherwise compromised, and who could benefit from a stronger immune response and more specifically enhanced activation of T-cells having increased motility. In particular, the invention significantly improves the body's immune response of patients afflicted with, for example, autoimmune diseases (e.g., type 1 diabetes, Addison disease, rheumatoid arthritis, multiple sclerosis, celiac disease, systematic lupus, Crohn's disease and chronic inflammatory demyolinating polyneurapathy (CIDP), cancer tumors mediated by active T cells, lung infection (e.g., such as Corona virus infection and pneumonia), HIV, upper respiratory infection (e.g., bronchitis and sinus infections) or a combination thereof.

Phototherapy has been harnessed to artificially provide the benefits of sunlight in situation where exposure to sunlight is sub-optimal. Thus, in winter for example, phototherapy is known to help alleviate or prevent seasonal affective disorder, a form of depression that that arises from prolonged lack of sunlight. Phototherapy can also provide sunlight to persons who otherwise lack exposure due to confinement, disability, or other causes. The use of phototherapy is not limited to compensating for sunlight exposure. Indeed, research has shown as even persons with sufficient sunlight exposure can benefit from additional sunlight that trigger a variety of response in the body that provide health benefits. Such benefits may include enhanced synthesis of vitamin D and stronger immune response.

Unlike other methods of providing phototherapy, which are generally directed to treating skin conditions, embodiments of the present invention are directed to treating internal conditions of the patient (conditions that affect organs other than the skin or other surface areas of the body though such conditions may also include skin and such surfaces). To that end, the systems and methods of the present invention employ high power sources of blue light to irradiate the patient, as opposed to lower power sources employed by other systems and methods of providing phototherapy. The high power blue light has been found to stimulate the release and motility of T-cells housed in the skin. The activation of T-cells housed in the skin floods the patient's bloodstream with newly motile T-cells, where the increased concentration facilitates T-cells attack of pathogens affecting internal organs (therefore organs not irradiated by the blue light). Indeed, the administration of blue light to the skin may increase T-cell motility by 300% and overall immune system efficiency by almost an order of magnitude. The increased immune response and specifically the activation of additional T-cells helps strengthen the immune system, fight off a variety of pathogens and treat various health conditions. In summary, embodiments of the present invention use T-cell activation by using high output, full body irradiance to provide a drug free method to bolster the body's immune system against various infections including those affecting internal organs. In addition to treating the aforementioned conditions, the method may provide the elderly and other vulnerable populations with an improved quality of life and greater longevity by fighting off and defending against pathogens that enter the body.

It is an object of embodiments of the present invention to provide light therapy to a patient that is equivalent to the blue light absorbed in 4 to 6 hours of summer sunlight using blue light sources. Preferably, two high power blue light sources are used. The light sources are configured to irradiate the entire surface area of the front and back side of the patient's body. The method is designed to provide an average irradiance or intensity of light of from about 70 watts/m$^2$ to about 140 watts/m$^2$ over the entire body. This requires powerful blue light sources positioned sufficiently close to the patient to deliver this amount of irradiance. The light is applied uniformly (or as near as possible) over the entire body of the patient below the head. Alternatively, the light may cover the head and face, in which case the patient can wear blackout glasses or goggles to protect the eyes. A typical treatment may consist of irradiating with blue light having a wavelength of about 450 nm and a wattage of about 210 W, for about 20 minutes. This has been found to provide sufficient energy to trigger an immune response strong enough to treat internal conditions. This treatment can be applied periodically, for example between several times a week to once a month based on the patient's needs, conditions, and characteristics, to address immuno dysfunctionality.

Figure 8:
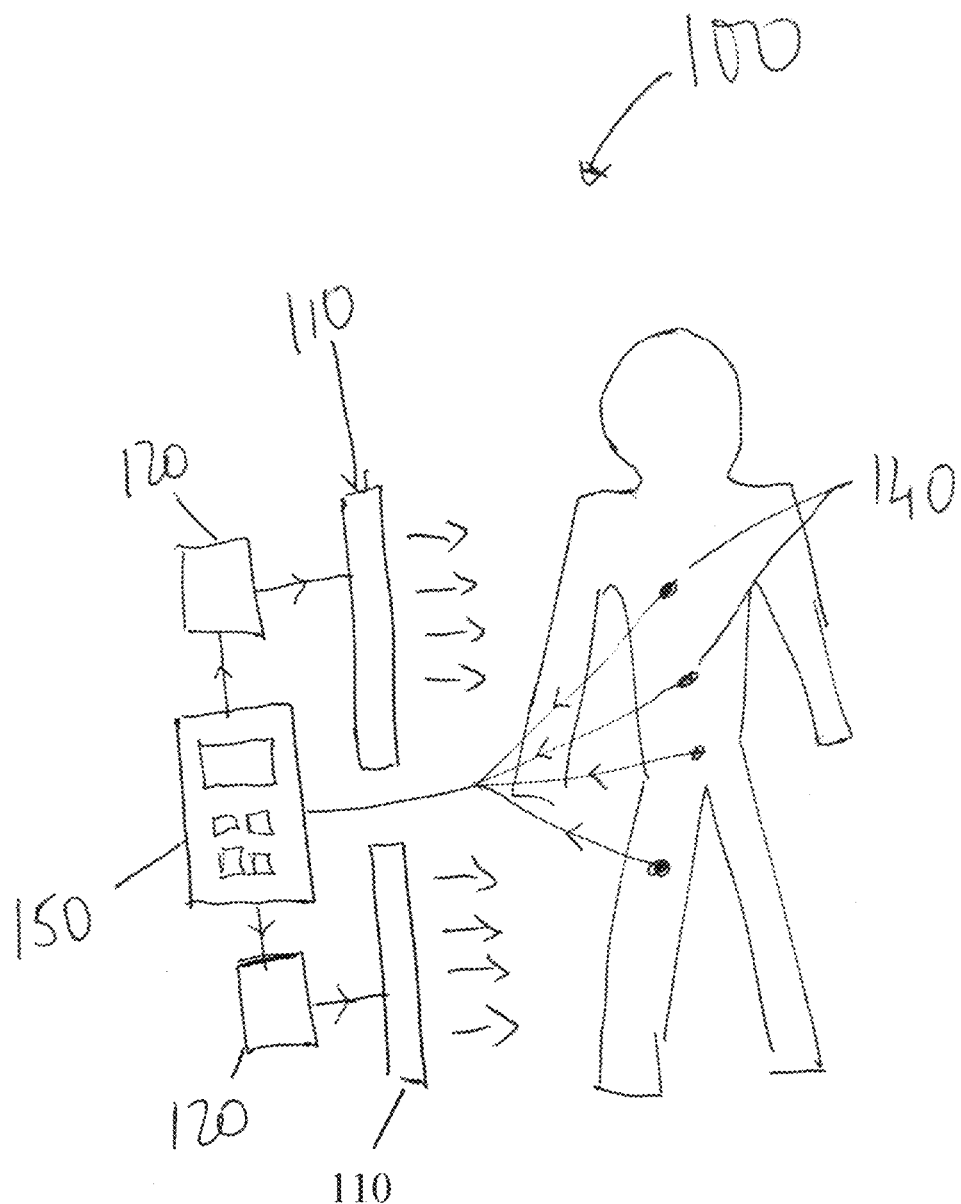
FIG. 8 illustrates a system diagram of an exemplary phototherapy system according to an embodiment of the present invention.

FIG. 8 illustrates a system diagram of an exemplary phototherapy system 100 according to an embodiment of the present invention. The phototherapy system 100 is configured to provide blue light phototherapy to a subject or patient. The blue light is calibrated to stimulate the immune system of the subject by stimulating T cell motility. Embodiments of the present invention may thus serve to treat various internal conditions by increasing the population or concentration of T-cells in the bloodstream, as well replicate the sun's positive effect on the body to address immune system disfunction and weakness.

The phototherapy system 100 comprises one or more light sources 110 configured to provide blue light to a patient. In FIG. 8, the one or more light sources consist of two linear LED lamps or LED baton lamps 110. The LED baton lamps 110 are configured to emit blue light to irradiate the subject. Each LED lamp 110 comprises an array of LEDs 115 configured to emit light in the wavelength of between about 400 nm and 490 nm. This range approximates the blue wave range of sun light, which has been found to provide a number of health benefits and immune system benefits. Preferably the LED batons lamps 110 are configured to emit 450 nm blue light or a range of wavelength narrowly centered at approximately 450 nm (e.g., about 400 nm to 490 nm or about 410 nm to 490 nm). As described above, 450 nm blue light have been found to be the optimal wavelength to stimulate the immune system and address potential disfunction and weaknesses.

Figure 9:
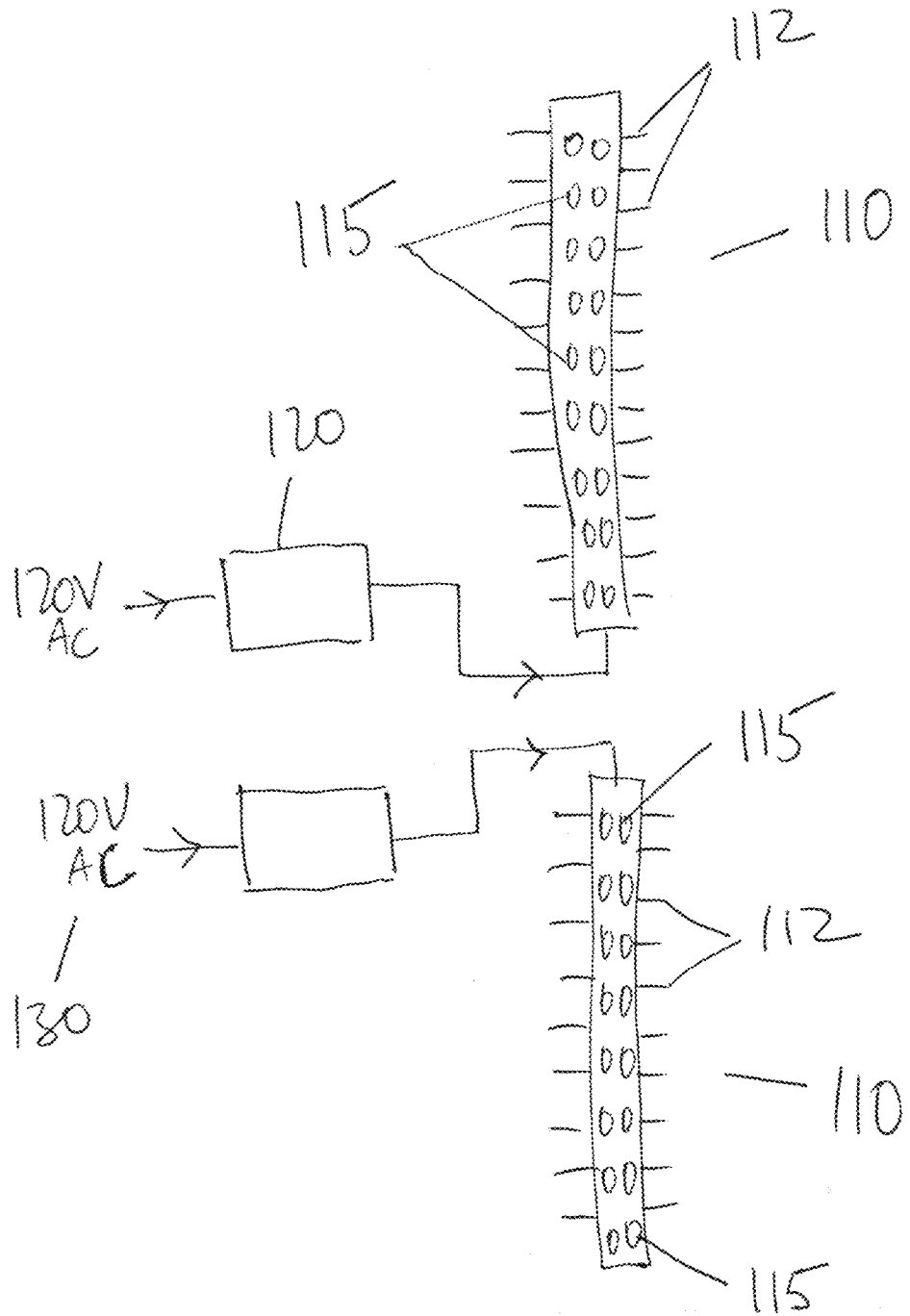
FIG. 9 illustrates the blue light system or generator of the phototherapy system according to an embodiment of the present invention.

FIG. 9 illustrates the blue light system or generator of the phototherapy system 100 according to an embodiment of the present invention. Each baton lamp 110 may comprise a plurality of LEDs lamps 115 each having a wattage of about 5 W. High power irradiation is preferred and necessary to provide the immune system benefits that the invention enables. High power irradiation further enables the baton lamps 110 to irradiate a wide surface of the patient's body, and further enables a combination or two or more baton lamps 110 to provide immune system boosting blue light to the entire body (i.e., front and back surfaces). Thus, in a typical embodiment, each blue light baton 110 may have a total wattage of about 210 Watts (or about 190 W to 230 W in some embodiments). Moreover, there is no upper limit to the wattage of the LED baton lamps 110. Instead, the combination of baton lamp power and duration of irradiation is configured to yield between about 1000 to about 4000 Watt-minutes of irradiance. Typical levels of desired irradiance are about 2500 Watt-minutes. The radiation energy that is actually to be absorbed will depend upon the patient's size and physiology, but these values have been proven to be optimum for various sized patients. Absorption also depends upon the lamp's power (wattage) and time of treatment. A typical treatment may consist of irradiating with blue light having a wavelength of about 450 nm and a wattage of about 210 W, for about 20 minutes. This has been found to provide sufficient energy to trigger an immune response strong enough to treat internal conditions. The phototherapy system 100 is configured to modulate the duration of irradiation based on the desired level of irradiance and the power of the LED baton lamps 110 (among other factors).

The baton lamps 110 of the phototherapy system 100 may be powered by drivers 120. The drivers 120 receive power from a power source 130. The power source 130 typically may be a standard AC power source such as from a wall outlet. The drivers 120 are configured to convert power received from the power source 130 into power for driving the LED baton lamps 110s, for example from outlet AC power to DC power required by the LED baton lamps. An exemplary power source 130 may provide any one of 120/208/240 VAC at 50/60 Hz as AC power. An exemplary driver 120 may be configured to receive as input any one or various combination of the AC power. Preferably, the driver 120 is configured to deliver about 210 Watts sufficient to power each baton lamp 110, for example 150-300 VDC at 700 mA.

For initial testing of the invention, two blue LED light sources 110 have been used with each having the following performance factors: 210 Watts, Radiant power of 105 watts at 450 nm wavelength. The wavelength distribution is preferably narrow, for example 99% at 450 nm. Beam pattern is Lambertain on a 22 inch (0.56 m) long light source emitting surface. The power source 130 or driver is 120 volt input with 240 Volts AC 50/60 Hz. And is self-grounded. Other lamps with lower or higher wattage can be used provided that they generate blue light, though high power lamps are preferred. The effectiveness of the phototherapy system 100 is enhanced when the LED baton lamps 110 operate in high output levels and are configured to apply the blue light as uniformly as possible. In appearance, they provide blue light similar to a fluorescent bulb's but bluer and more intense. The blue LED lamps 110 can be provided as any type of bulb, including Reflector and Par lamp configurations as well as tube lamps or baton lamps, provided that they have sufficient power. Lighting suppliers can custom manufacture some of the more conventional designs having the necessary specifications and performance requirements upon request.

The LED baton lamp 110 has the length in the range of about 23 to 25 inches. The exemplary lamp batons 110 illustrated in FIG. 2 are about 24 inches long and about 5½ inches wide. The batons 110 are longitudinally aligned and separated by a distance or gap of approximately 4 inches. In some embodiments, the lamp batons are oriented longitudinally along the height of the subject with at least two baton lamps aligned with the subject's upper torso and with at least two baton lamps aligned with the subject's legs with the lamps arranged about 7.62 cm to 30.48 cm (3 to 12 inches) from the subject's skin. These dimensions are arrangements are configured to provide broad, even, and sufficiently powerful irradiation of blue light over the entire body of the subject to be treated. Other dimensions, spatial arrangements, and spacing of the lamp batons 110 are possible provided that the radiation amount and intensity applied to the subject remains within the aforementioned parameters (e.g., sufficient to stimulate the release of T cells and provide immune system benefits).

In some embodiments, the high power of the lamp batons 110 may cause the lamps to overheat and requires means of mitigating or preventing the excess heat. Cooling mechanisms may be provided to dissipate heat generated by the high-powered LEDs and avoid harming the patient, as the baton may be positioned close to the patient's skin in some embodiments. Exemplary cooling mechanism include heat sinks, fans, cooling fins (FIG. 2), or any other cooling device or scheme that can be utilized with the baton lamps. In some embodiments such as illustrated, the cooling fins 112 measuring about two inches long are provided along the length of the lamp batons 110 and serve to dissipate excess heat resulting from the high powered LEDs of the batons.

Figure 10:
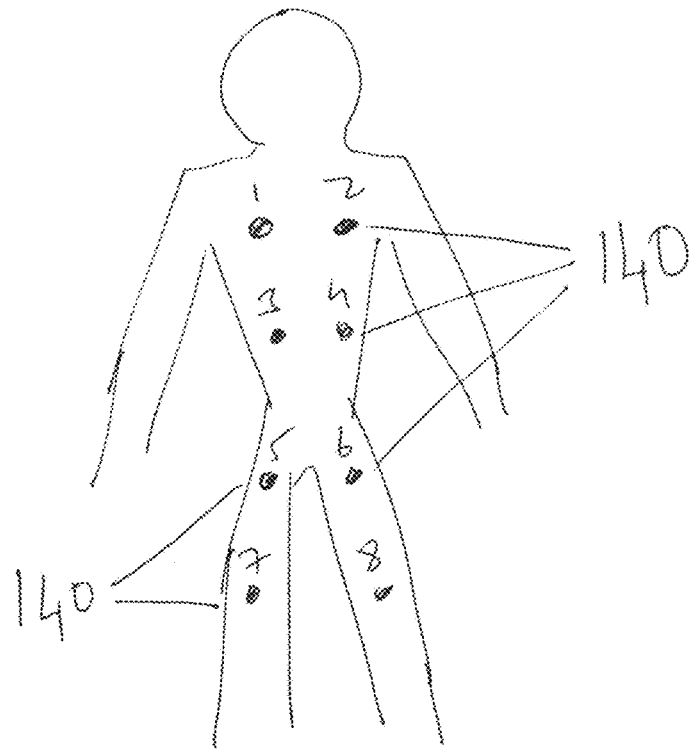
FIG. 10 illustrates an exemplary patient having a plurality of light sensors mounted on the patient for measuring irradiation levels.

The phototherapy system 100 further comprise a plurality of blue light sensors 140 configured for mounting on the patient. The number of sensors may vary but typically the sensors 140 number between 8 and 12 and are provided to measure and provide irradiance value on the skin. Monitoring the level of irradiance on the skin is critical to treating patient effectively and with proper efficacy and preventing the delivery of excess irradiation. In particular, the sensors 140 enable the calculation or adjustment of irradiance levels and dwell levels to obtain the appropriate amount of light for the patient. To that end, the light sensors 140 are strategically positioned and spaced a part on the body of the patient. FIG. 10 illustrates an exemplary patient having a plurality of light sensors 140 mounted on the patient for measuring irradiation levels. A pair of sensors 140 is mounted on each of the upper chest, lower chest, stomach, and mid-thigh. Each pair is arranged horizontally such that at each of the aforementioned parts of the body, a sensor 140 is positioned on the left side and on the right side. Each thigh receives its own sensor 140. The sensors 140 are placed in locations whose aggregate measurements will provide an accurate reading of the amount of light applied to the patient. Although the plurality of sensors 140 illustrated is installed on front side of the body of the patient, other configurations are possible, such as a plurality of sensors 140 installed on the back of the patient, or distributed both on the front and back, or even sides, in some embodiments. The optimal distribution of sensors on the patient may be related to the position and number of light sources, in some embodiments.

The phototherapy system 100 further includes a controller 150. The controller 150 is configured to control operation of the phototherapy device 100. In particular, the controller is coupled to the baton lamps or the drivers of the baton lamps and is configured to control their operation (i.e., on or off). Further, in some embodiments, the controller is configured to vary the intensity of the light emitted by each lamp. The controller 150 is further coupled to the sensors 140, which feed it light level measurements. In particular, the sensors 140 feed into a photometer 145 housed in the controller 150. The photometer 145 is configured to receive and process sensor data. The controller 150 may have or be coupled to a user interface that enables an operator to control the operation of the phototherapy system 100. The controller 150 may be a control panel, a computer, a handheld remote device, or any other device that enables a user operating the phototherapy system 100 to control its operation.

Figure 11:
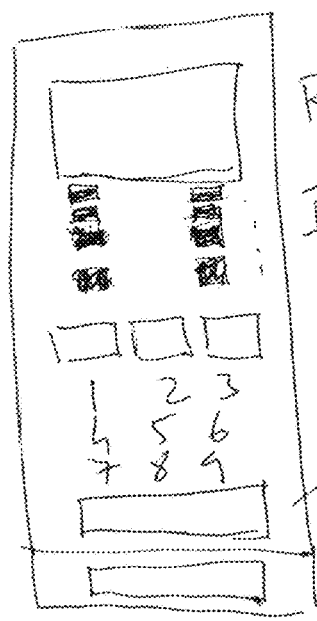
FIG. 11 illustrates an exemplary controller, according to an embodiment of the present invention.

FIG. 11 illustrates an exemplary controller 150, according to an embodiment of the present invention. In the embodiments, illustrated the controller 150 is a remote controller. The control device 150 includes an input device and one or more displays. The input device may be a set of buttons, a keyboard, or any other input devices. The input device enables the user to set up and configure the phototherapy system and control its operation. The displays provide readout of various values associated with the phototherapy system 100 and received therefrom. The controller 150 may be in wired or wireless communication with an onboard controller on the phototherapy system.

The controller 150 can display irradiation readouts for each of the sensors 140 distributed over the patient's body. In the embodiment illustrated, eight sensors 140 are installed on the patient and readouts therefrom are provided to the controller 150 and displayed thereon in Watts/m$^2$. Signals from each sensor 140 may be received by the controller 150 on a continuous or periodic basis. In some embodiments, the controller 150 may poll each sensor 140 periodically to obtain the irradiation readout at its location. The individual irradiation levels received from each of the skin-mounted sensors can be used to help align the patient to maximize irradiance in all the sensor locations. For example, in the embodiments illustrated in FIG. 10, where the sensors are affixed to the patient, the sensor readings on the controller may show during testing or treatment that the sensors on the left side of the body are receiving less light than those on the right side of the body. The patient may as a result be requested to adjust their position (for example rotate their left side toward the baton lamps) in order to even out their exposure. The operator may monitor the sensor readings on the controller 150 during the adjustment until the desired values are obtained from the relevant sensors 140.

The controller 150 may also provide the average amount of irradiation received by the patient. This is obtained by averaging the values detected by the plurality of sensors 140 installed on the patient during treatment. The controller 150 further enables the operator to configure the phototherapy system and input a set of treatment parameters for a treatment session using the input device. The operator may input patient information such as sex, weight, height, and other information relevant to the blue light treatment. In some embodiments the input may also include the posture of the patient, for example whether the patient is standing, seated, lying down, etc. (A seated patient may require greater treatment times or duration of exposure to the blue light than a standing patient, for example). The phototherapy system 100 use this data (among others) to dynamically control and adjust the treatment parameters for the patient, such as irradiation target values and treatment time or schedule or pattern, in response to the sensor during the period in which the patient is being treated. An irradiation pattern may include alternating periods of irradiation time and rest time (when the lamps are off and not illuminating the patient). For example, it may be determined that that the patient should be illuminated for 5 minutes followed by 3 minutes of rest time and another 5 minutes of irradiation. The controller 150 may also enable the operator to set the irradiation target value, treatment time, and other relevant parameters for treatment based on the patient's needs. Typical target irradiation levels are about 2500 Watt-Mins, and can range from 1000 to 4000 Watt-Mins. Irradiation target value may be computed for each side of the body, in some embodiments.

In some embodiments, light readings or measurements from the plurality of sensors 140 are received by the phototherapy system 100 as feedback for automatically adjusting the blue light output to match a target level of illumination during treatment. The controller 150 may monitor one or more sensors on a continuous basis or at frequent intervals. Specifically, the controller 150 may receive a continuous or perioding signal for an irradiance level from one or more sensors 140. The closed loop configuration enables the controller 150 to dynamically vary the light output from the light sources or baton lamps based on the received sensor values to match potentially changing conditions during treatment. The controller 150 may accomplish this by controlling the light output in a variety of manners. The controller 150 may switch the lamps on or off or pulse the light sources based on the sensor readings in some embodiments. In some embodiments, the controller 150 is configured to vary an intensity of the light output (i.e., make the lamps brighter or less bright) based on the sensor input to the controller 150, in some embodiments. In an exemplary situation, although patients are typically instructed to minimize motion during treatment, they may inadvertently move toward or away from the baton lamps 110. The sensor readings (such as an average of the sensor values) may vary according to the position of the patient or other conditions in the photometric chamber, prompting the phototherapy system to dynamically increase or decrease illumination from the batons 110 in response to compensate for change in intensity and maintain the target irradiation or intensity (such as from about 70 watts/m² to about 140 watts/m²) necessary to activate the immune system benefits.

A variety of configurations are provided as mounting structures, housing, or enclosure for the baton lamps 110. Generally, the light sources 110 can be mounted onto or incorporated into an enclosure which is configured to surround the patient so that all sides of the patient's body are treated simultaneously. The lamps may be spaced out on an interior surface of the structure to facilitate directing the blue LED light at all body surfaces. The structure can be a polygonal, oval or cylindrical chamber or enclosure that is either closed or open at the top. Preferably, the enclosure does not extend above the head of the person to be treated to minimize concerns of eye damage from light exposure. Alternatively, the lamps 110 can be positioned only adjacent the patient's upper torso and legs. Typically, an interior surface of the structure (where the patient is positioned during treatment) is lined with a reflective material such as aluminum foil, in some embodiments. The reflective material is configured to reflect or bounce the light emitted by the baton lamps onto the patient, and to ensure uniform illumination around the body of the patient by all the available light.

Figure 12:
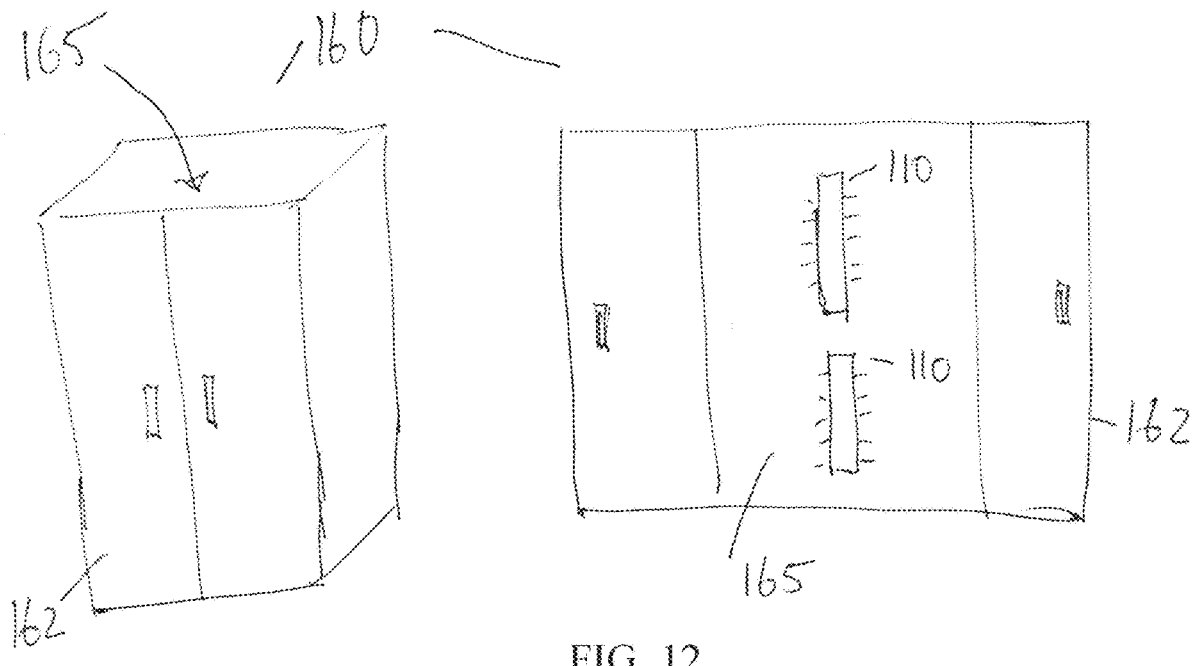
FIG. 12 illustrates an exemplary cabinet or wall unit, according to an embodiment of the present invention.

FIG. 12 illustrates an exemplary cabinet 160 or wall unit, according to an embodiment of the present invention. The cabinet 160 may be a rectangular enclosure having a door 162 (e.g., similar to a small closet). The interior of the enclosure or housing comprises the photometric chamber 165 and constitutes the treatment site of the patient. The dimensions of the enclosure 160 or housing and of the photometric chamber 165 inside are wide enough to enable a patient to stand comfortably or rotate without coming in contact the walls. In this embodiment, a pair of baton lamps 110 are mounted in an interior surface of the photometric chamber so that the patient's entire body is illuminated by the baton lamps 110. To that end, the baton lamps 110 are aligned along a vertical line (one baton lamp above the other) and separated from each other by a few inches. Preferably, the lamps 100 are oriented longitudinally along the height of the subject. Thus, the lamps 110 are oriented vertically when the subject is standing up or sitting and horizontally in configurations where the subject is laying down, as enabled by other variations of the enclosure 160.

In some embodiments, the lamps 110 can be mounted in a circular or oval photometric chamber which surrounds a standing patient. Part of the chamber acts as a door to allow the subject to step inside before energizing the lamps. Although some subjects may not be comfortable standing in a relatively snug chamber, this embodiment provides maximum radiation exposure and minimum treatment times.

Figure 13:
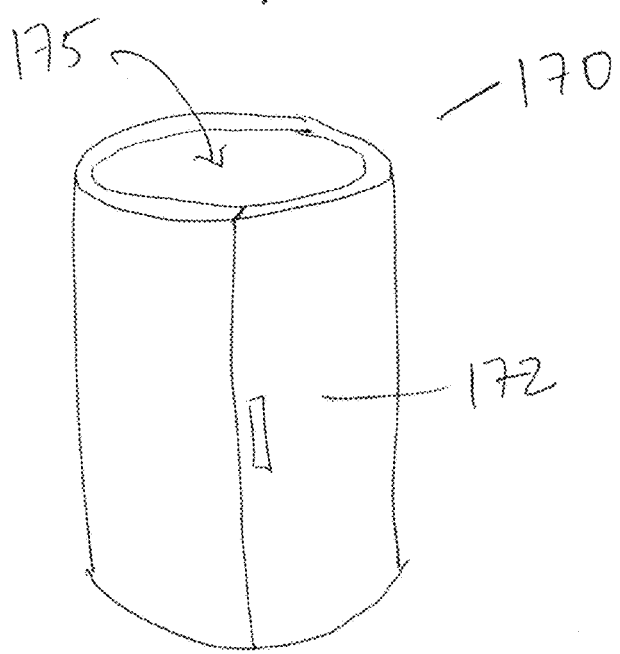
FIG. 13 illustrates another exemplary cabinet, according to an embodiment of the present invention.

As shown in FIG. 13, a cylindrical enclosure 170 may be provided, in some embodiments. This enclosure 170 can include a door 172 or movable panel 172 that enables the patient to enter the enclosure 170. The LED lamps 110 may be mounted in uniformly spaced locations on the internal surface of the enclosure 160 so that the patient's entire body is illuminated with the blue LED light. In a preferred embodiment, the enclosure's height does not exceed that of the patient. Typically, a height of about 5 feet is acceptable. A small platform or stool may be provided inside chamber 175 to raise shorter patients' heads above the enclosure to prevent irradiation damage to the eyes. Alternatively, the enclosure 170 can be configured to be raised or lowered to conform to the height of the individual patient to be treated. The interior 175 of the enclosure may be lined with reflective material.

The cylindrical enclosure or chamber 170 of FIG. 13 includes a wall member that provides the enclosure, access to which is provided by door 172 which can be opened by a handle. As noted herein, a square rectangular or other polygonal shaped enclosure can also be used. The lamps can be mounted on the interior surface of the chamber so that when illuminated all body surfaces of the patient standing therein would be exposed to the blue LED light radiation.

In some embodiments, the door may be a sliding door or a curtain.

In an embodiment, a patient may stand in front of the batons 110 to expose the front side of the body and then turns around to expose the back side of the body to the light source. While the patient's skin is exposed to the LED light radiation, their eyes must be protected from the LED lights with material that shields the eye from the light such as dark sunglasses with heavy tint or non-transparent material, or by a blindfold that is capable of shielding the subject's eyes from the light. Additionally, the lamps may be typically mounted on a structure or structures that do not extend above the neck of the patient to minimize the irradiation of the patient's face and eyes. Alternatively, the lamps may cover the head and face, in which case the patient can wear blackout glasses or goggles to protect the eyes.

In some embodiments, instead of being mounted on a support, the photo-therapy device 100 (or more specifically the baton lamps 110) can be attached to a wall with a connection that allows the support surface to be pivoted to be adjacent a table or a bed for exposure to the person when the person is lying down. It is understood that other mounting configurations for the baton lamp and configurations for a photometric chamber or enclosure are possible.

Preferably, the baton lamps 110 are positioned substantially parallel to the side of the patient's body they are facing (e.g., with the front of the body) and the distance between the baton lamps is calculated to provide uniform illumination (and irradiance) on the skin of the patient. In some embodiments, the blue light sources and the patient are separated by between about 7.62 cm to 30.48 cm (3 to 12 inches).

Patients to be treated using the phototherapy system of the present invention should be undressed or in cotton garments during treatment. This enables minimal blockage of blue wavelength light emitted by the baton lamps 110. Depending on the configuration of the enclosure, if any, as well as the power of the baton lamps, the patient may stand or sit. A stool is provided for that purpose. Regardless of the patient's position, care should be taken to prevent or minimize irradiation of the patient's eyes either by positioning the patient's head away from the light and/or by shielding the eyes with a cover such as heavily tinted sunglasses, a blindfold, or an opaque material. As previously noted, sensor placement on the body may be adjusted based on the posture of the patient to ensure that irradiation over the entirety of body (below the head) can be adequately measured or approximated.

In some embodiments, a method for activating T cells in a subject in need thereof is provided. The method comprises applying blue LED light radiation to exposed skin surfaces of the subject. The radiation is applied to the exposed skin surfaces of at least the subject's upper torso including both front and back sides by a plurality of blue light generating lamps each having a wattage of at least about 5 watts for a total exposure time of at least about 10 minutes. The emitted blue light has a wavelength in the range of between about 400 and 490 nm. At least about 250 watts-minute of the blue light radiation is applied to the subject. Preferably, at least about 10 minutes of continuous radiation is applied per side of the body for the radiation treatment. The higher the wattage, the shorter the duration of the radiation. Such total radiation can be repeated for 3 to 15 treatments, depending on the wattage of radiation. In desired embodiments, 2 or 4 LED lights each having over about 15 watts are used and preferably each being about 50 to about 200 watts per LED light source. After applying the radiation, a serum concentration of a T cell marker increases in the subject. In some embodiments, the T cell marker is Interferon Gamma (IFN-γ). In some embodiments, the subject suffers from skin rash. The rash may be present on the subject suffering from Bullous pemphigoid, Lichen planus, porokeratosis, Grover's disease or diseases which are associated or co-existent with Grover's disease. In other embodiments, the subject suffers from an internal medicine condition. The condition may comprise autoimmune diseases, cancer tumors mediated by active T cells, lung infection, HIV, upper respiratory infection or a combination thereof. The autoimmune diseases may comprise type 1 diabetes, Addison disease, rheumatoid arthritis, multiple sclerosis, celiac disease, systematic lupus, Crohn's disease, chronic inflammatory demyolinating polyneurapathy (CIDP) or a combination thereof. The lung infection may comprise Corona virus infection, pneumonia or a combination thereof. The upper respiratory infection may comprise sinus, bronchitis, throat infections or a combination thereof.

EXAMPLES

The following examples illustrate the benefits and advantages of the present invention.

Example 1. Radiation Measurements

The levels of exposure of radiation of the LED light for different locations at different distances from the LED light source were measured. Blue light radiation was provided with four LED baton lamps. Each lamp had wattage of 35-40 watts and emitted light in wavelength range of from 410 to 490 nm with the center of the spectrum at 450 nm. The baton lights were approximately 2 feet long and attached to a wall arranged as shown in FIG. 6. These lights include a power cord which is liked to a power source that is plugged into a conventional 120 V wall outlet. The power source provides the necessary wattage for the lamps. FIG. 6 also shows different location points which were identified for radiation measurement. Table 1 shows the typical reading at three different distances from the LED light source for six different locations (A, B, C, D, E and F).

When the distance from the LED light source was at least 25.4 cm (10 inches), the radiation measurements for the six different locations (i.e., locations A, B, C, D, E and F) reached similar levels with equal exposure.

TABLE 1

Radiation measurements in watts per meter squared (W/m$^2$)

| Location | Radiation at different distances from light source (W/m$^2$) | | |
| --- | --- | --- | --- |
| | 10.16 cm (4 inches) | 15.24 cm (6 inches) | 25.4 cm (10 inches) |
| A | 40 | 31 | 23 |
| B | 52 | 35 | 23 |
| C | 42 | 29 | 22 |
| D | 44 | 36 | 24 |
| E | 29 | 28 | 24 |
| F | 34 | 32 | 23 |
| Average radiation | 40.2 | 31.8 | 23.5 |

Example 2. Blue LED Light Exposure for Treating Grover's Disease

Blue light radiation was provided with four LED baton lamps. Each lamp had wattage of 35-40 watts and emitted light in wavelength range of from 410 to 490 nm with the center of the spectrum at 450 nm. Each of the LED baton lamp was approximately 2 feet long and attached to a wall in the arrangement shown in FIGS. 1B and 6. The skin of the patient with Grover's disease was exposed to the LED light radiation. Eyes of the patient were protected from the LED lights, such as wearing sunglasses with heavy tint or non-transparent material. The patient stood in front of the LED lights and exposed the skin of the body for both sides, i.e., front and back sides of the body. The exposed skin is at the distance of 25.4 cm (10 inches) from the LED light source. Different exposure times of from 10 to 40 minutes were tested. The skin in back and front sides of the body was exposed to the LED light source in an equal length of time.

The status of the skin was improved after the LED light exposure. The presence of rash was dramatically reduced from one that presented multiple raised red lesions before the treatment to one having only one or two small pink lesions after the LED light exposure. The exposure of the LED light was very effective in the treatment of the skin of the patient with Grover's disease, when sufficient energy reached the skin, preferably at the distance of 25.4 cm (10 inches) for about 22 minutes for each side of the body, i.e. the front and back sides of the body.

In comparison, previous treatments of the subject using conventional pharmaceuticals provided no measurable improvement in skin status.

Example 3. Blue Fluorescent Light Exposure for Treating Grover's Disease

Nine patients (Caucasian males, over age 50) suffering from Grover's disease was treated with blue light radiation with seven 1.5 feet continuous wave fluorescent batons, each lamp having wattage of 32 watts. All subjects were provided opaque safety goggles and subsequently underwent non-ionizing blue light phototherapy irradiation which lasted 16 minutes in duration, eight minutes for each side of the torso to ensure even application, three times a week for five continuous weeks for a total of 15 treatments. Target irradiance was 14 mW/cm$^2$ with a total dose of 10 J/cm$^2$ delivered over the 16 minutes and cumulative dosage given was 160 J/cm$^2$.

Figure 14A:
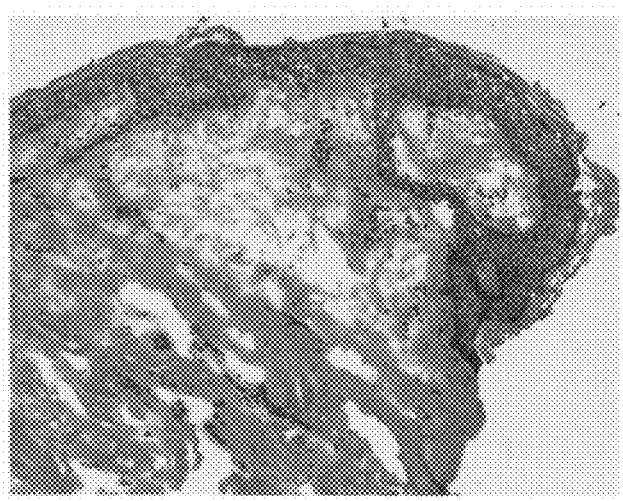
FIGS. 14A-14C illustrate histology images of skin of a patient with Grover's disease before the blue light radiation treatment, according to an embodiment of the present invention.
Figure 14B:
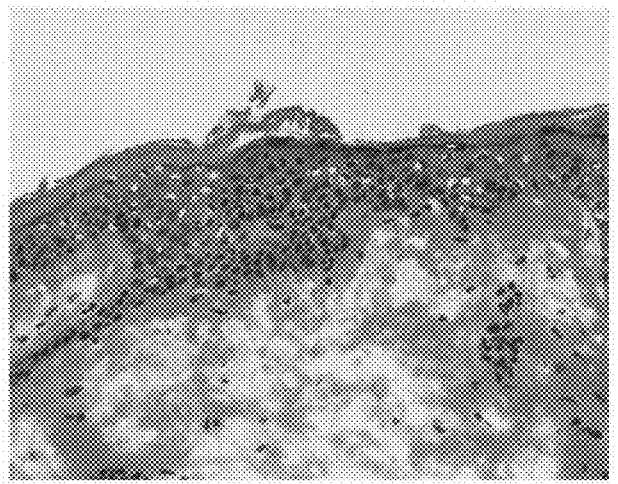
Figure 14C:
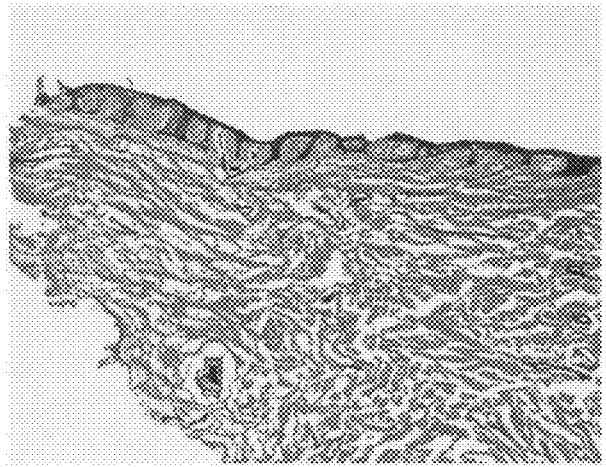
Figure 14D:
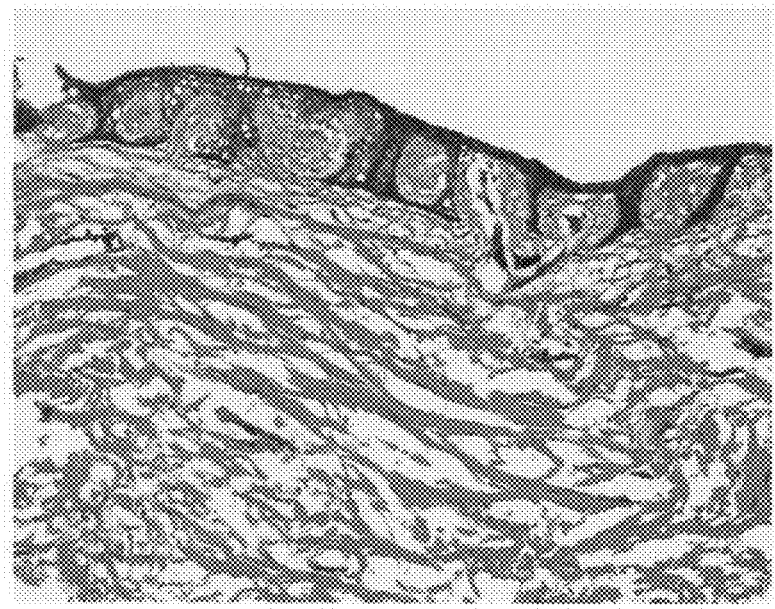
FIGS. 14D-14E illustrate histology images of skin of a patient with Grover's disease after the blue light radiation treatment, according to an embodiment of the present invention.
Figure 14E:
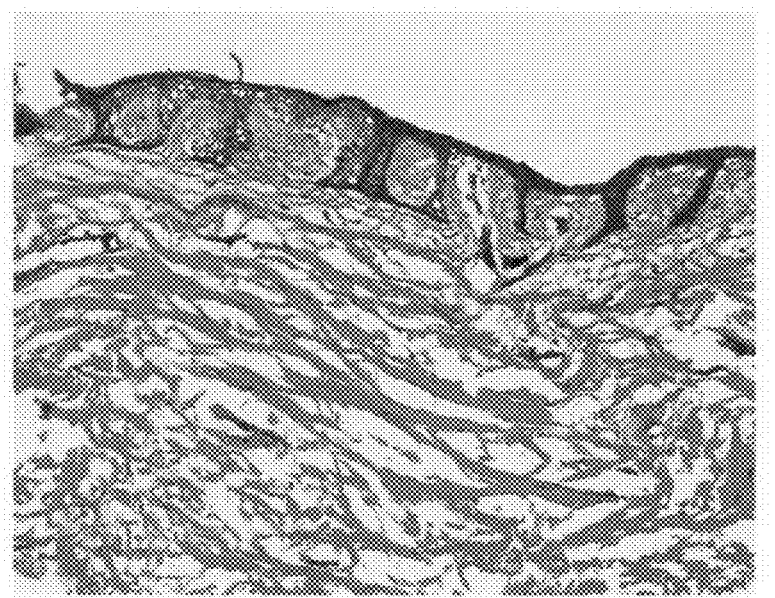

Before (as shown in FIGS. 14A-14C) and after the treatment (as shown in FIGS. 14D-14E), histology images of skin of the patients were taken and compared. The histology changes suggest that the blue light therapy reduced hyperkeratosis in the stratum corneum (uppermost layer) of the skin. This also showed some evidence of less acanthosis. Furthermore, the histology changes showed reduction of epidermal proliferation and thickening with evidence of less immune cell penetration in the epidermis, specifically T-cell lymphocytes. From the histology images, no evidence of dermal related ranges was noted. This included no evidence of vascular changes, inflammation, or collagen changes.

It is noted that a system with LED lights should outperform the system with fluorescent lights described here in terms of treating Grover's disease. This is because LED lights are twice as efficient as fluorescent lights so twice as much light in LED lights at same wattage. Also, LED lights degrade at a far slower rate than fluorescent lights.

Example 4. Blue Light Exposure for Treating Grover's Disease and Upper Respiratory Infection 68 year old male patient was treated initially 3 times for total time of 54 minutes in the first year of blue light therapy for Grover's disease with a system having two linear LED lamps 210 watts each. The system is designed to operate with patient standing or sitting with the irradiated blue light applied for a total of ~20 minutes standing (10 minutes front side & 10 minutes back side). This system is designed to provide an average irradiance of about 70 watts/m² over the entire body. Grover's disease is a recurring disease and patient would have one treatment when itch or early stage rash blotches occurred. Those treatments were about 18 minutes every few weeks during winter months (when not exposed to sun for long periods such as golfing). The patient noticed his frequency of upper respiratory infections such as sinus, bronchitis and sore throats were greatly reduced. Upon further analysis of his medical records, the frequency for needing physician care for upper respiratory diseases for 3 years cumulatively after starting blue light treatment was reduced 67%, compared to the counterpart for 3 years before the patient started using the blue light therapy. The patient was not taking any other forms of medicine or treatment other than the blue light therapy during this 6 year period.

Example 5. Blue Fluorescent Light Exposure for Activating T Cells

Four patients (Caucasian males, over age 50) suffering from Grover's disease were treated with blue light radiation with seven 1.5 feet continuous wave fluorescent batons, each lamp having wattage of 32 watts. All subjects were provided opaque safety goggles and subsequently underwent non-ionizing blue light phototherapy irradiation which lasted 16 minutes in duration, eight minutes for each side of the torso to ensure even application, three times a week for five continuous weeks for a total of 15 treatments. Target irradiance was 14 mW/cm² with a total dose of 10 J/cm² delivered over the 16 minutes and cumulative dosage given was 160 J/cm².

Before and after the treatment, the serum concentration of Interferon Gamma (IFN-γ) in patients with Grover's disease was measured. Post-treatment serum IFN-γ level (3.18±1.44 pg/mL) was significantly higher (i.e., about 27% higher) than pre-treatment serum IFN-γ level (2.50±0.68 pg/mL). IFN-γ is one of T cell markers because T cells predominantly secrete IFN-γ. Thus, the substantial increase of serum IFN-γ level after the treatment indicates T cell activation in the patients.

It is noted that a system with LED lights should outperform the system with fluorescent lights described here in terms of activating T cells. This is because LED lights are twice as efficient as fluorescent lights so twice as much light in LED lights at same wattage. Also, LED lights degrade at a far slower rate than fluorescent lights.

It is to be understood that the present invention is not to be limited to the exact description and embodiments as illustrated and described herein. To those of ordinary skill in the art, one or more variations and modifications will be understood to be contemplated from the present disclosure. Accordingly, all expedient modifications readily attainable by one of ordinary skill in the art from the disclosure set forth herein, or by routine experimentation therefrom, are deemed to be within the true spirit and scope of the invention as defined by the appended claims.

What is claimed is:

1. A method for treating an internal medical condition affected by a subject's immune system response involving T cells, the method comprising:
   applying blue LED light radiation to exposed skin surfaces of the subject,
   wherein the blue LED light radiation is uniformly applied to the exposed skin surfaces of at least the subject's upper torso including both front and back sides by a plurality of blue LED light generating lamps each having a wattage of at least about 15 watts for a total exposure time of at least about 10 minutes per each of the both front and back sides, with the emitted blue light having a wavelength in the range of between about 410 and 490 nm, so that at least about 250 watts-minute of the blue LED light radiation is applied to the subject.

2. The method of claim 1, wherein the condition comprises autoimmune diseases, cancer tumors mediated by active T cells, lung infection, HIV, upper respiratory infection or a combination thereof.

3. The method of claim 2, wherein the autoimmune diseases comprise type 1 diabetes, Addison disease, rheumatoid arthritis, multiple sclerosis, celiac disease, systematic lupus, Crohn's disease, chronic inflammatory demyelinating polyneuropathy (CIDP) or a combination thereof.

4. The method of claim 2, wherein the lung infection comprises Corona virus infection, pneumonia or a combination thereof.

5. The method of claim 2, wherein the upper respiratory infection comprises sinus, bronchitis, throat infections or a combination thereof.

6. The method of claim 1, wherein the blue LED light generating lamps each have a wattage of about 25 to 60 watts or about 35 to 50 watts and at a total exposure time of about 15 to 100 minutes or about 25 to 50 minutes.

7. The method of claim 1, wherein the blue LED light generating lamps each have a wattage of about 175 to 210 watts and at a total exposure time of about 20 minutes.

8. The method of claim 1, which further comprises placing the blue LED light generating lamps at about 3 to 12 inches away from the subject's skin.

9. The method of claim 1, wherein at least about 600 watts-minute or at least about 1200 watts-minute of the blue LED light radiation is applied to the subject.

10. The method of claim 1, wherein about 2500 watts-minute or between about 1000 and 4000 watts-minute of the blue LED light radiation is applied to the subject.

11. The method of claim 1, wherein the blue LED light radiation is applied to an entire surface area of a front and back side of the subject's body.

12. The method of claim 1, wherein the subject stands or sits during the treatment.

13. A method for activating T cells in a subject in need thereof, comprising:
applying blue LED light radiation to exposed skin surfaces of the subject,
wherein the blue LED light radiation is uniformly applied to the exposed skin surfaces of at least the subject's upper torso including both front and back sides by a plurality of blue LED light generating lamps each having a wattage of at least about 15 watts for a total exposure time of at least about 10 minutes per each of the both front and back sides, with the emitted blue light having a wavelength in the range of between about 410 and 490 nm, so that at least about 250 watts-minute of the blue LED light radiation is applied to the subject, and
wherein a serum concentration of a T cell marker increases in the subject after applying the radiation.

14. The method of claim 13, wherein the T cell marker is Interferon Gamma (IFN-γ).

15. The method of claim 13, wherein the subject suffers from skin rash.

16. The method of claim 15, wherein the skin rash is present on the subject suffering from Bullous pemphigoid, Lichen planus, porokeratosis, Grover's disease or diseases which are associated or co-existent with Grover's disease.

17. The method of claim 13, wherein the subject suffers from an internal medical condition.

18. The method of claim 17, wherein the condition comprises autoimmune diseases, cancer tumors mediated by active T cells, lung infection, HIV, upper respiratory infection or a combination thereof.

19. The method of claim 18, wherein the autoimmune diseases comprise type 1 diabetes, Addison disease, rheumatoid arthritis, multiple sclerosis, celiac disease, systematic lupus, Crohn's disease, chronic inflammatory demyelinating polyneuropathy (CIDP) or a combination thereof.

20. The method of claim 18, wherein the lung infection comprises Corona virus infection, pneumonia or a combination thereof.

21. The method of claim 18, wherein the upper respiratory infection comprises sinus, bronchitis, throat infections or a combination thereof.

* * * * *